US007074908B2

(12) United States Patent
D'Azzo et al.

(10) Patent No.: US 7,074,908 B2

(45) Date of Patent: Jul. 11, 2006

(54) PROTEIN SPECIFIC FOR CARDIAC AND SKELETAL MUSCLE

(75) Inventors: Alessandra D'Azzo, Memphis, TN (US); Antonella Bongiovanni, Memphis, TN (US); Tommaso Nastasi, Memphis, TN (US)

(73) Assignee: St. Jude Children's Research Hospital, Memphis, TN (US)

(*) Notice: Subject to any disclaimer, the term of this patent is extended or adjusted under 35 U.S.C. 154(b) by 246 days.

(21) Appl. No.: 10/014,774

(22) Filed: Oct. 29, 2001

(65) Prior Publication Data

US 2002/0099173 A1 Jul. 25, 2002

Related U.S. Application Data

(63) Continuation of application No. PCT/US00/11900, filed on Apr. 28, 2000.

(60) Provisional application No. 60/131,814, filed on Apr. 29, 1999.

(51) Int. Cl.

| | |
|---|---|
| ***C07H 21/02*** | (2006.01) |
| ***C12N 1/20*** | (2006.01) |
| ***C12N 15/00*** | (2006.01) |
| ***C07K 1/00*** | (2006.01) |

(52) U.S. Cl. ............ 536/23.1; 435/252.3; 435/252.32; 435/320.1; 530/350

(58) Field of Classification Search ............ 435/252.3, 435/252.32, 320.1; 536/23.1

See application file for complete search history.

(56) References Cited

U.S. PATENT DOCUMENTS 5,643,758 A * 7/1997 Guan et al. ................ 435/69.7

OTHER PUBLICATIONS

Nakamura et al. Oncogene. Feb. 26, 1998; 16(8):1009-19.*
Prinos et al. Teratology, (Feb. 1998) 57 (2) 108.*
Lee et al. Accession AA800025. Jul. 19, 1995.*
Nakamura et al., Oncogene, 1998; 16(8):1009-1019.
Price et al., EMBO J., 1993; 12(6):2411-2418.
Hartenstein et al., Development, 1992; 116(4):1203-1220.
Bridgeman, A., EMBL Database, Accession No. HS337018, Apr. 27, 1997, XP002145228.
Luo et al., Mol. Cell. Biol., 1997; 17(10):6057-6067.
Okazaki et al., The Journal of Biological Chemistry, 1996; 271(36):22052-22057.
Lee, N.H., "est189522", EMBL Database, Accession No. AA800025, Feb. 11, 1998, XP002145237.
Strausberg, R., "est," EMBL Database, Accession No. A1589199, Apr. 26, 1999, XP002145238.
Rottier, et al. ,DNA and Cell Biology, 1997; 16(5):599-610.
Hilton t et al., Proc. Natl. Acad. Sci. USA, 1998; 95:114-119.
Starr et al., Nature, 1997; 387:917-921.
Johnston et al., The Journal of Cell Biology, 1998; 143(7):1883-1898.
Iwai et al., PNAS, 1999; 96(22):12436-12441.
Boulianne et al., EMBO Journal, 1991; 10(10):2975-2983.
Corbin et al., Cell, 1991; 67:311-323.
Martin-Bermudo et al., Development, 1995; 121:219-224.
Zhou et al., Genome, 1994; 37:840-847.
Giljart, N.J., et al., "Expression of cDNA Encoding the Human "Protective Protein" Associated with Lusosomal B-Galactosidase and Neuraminidase; homology to Yeast Proteases" Cell 54:755-764 (1988).
Giljart, N.J., et al., "Mouse "Protective Protein" cDNA Cloning, Sequence Comparison and Expression" J. Biol. Chem. 265:4678-4684 (1990).
Wiegant, J., et al., "The Gene Encoding Human Protective Protein (PPGB) is on Chromosome 20" Genomics, 10:345-349 (1991).
Williamson, C.M., et al., "Protective Protein for B-galactosidase, Ppgb, Maps to the Distal Imprinting Region of Mouse Chromosome 2 but is Not Imprinted", Genomics, 22:240-242 (1994).
Shimomoto, M., et al., "A Human Protective Protein Gene Partially Overlaps the Gene Encoding Phospholipid Transfer Protein on the Complementary Strand of DNA" Biochem Biophys Res Comm 220:802-806 (1996).
Bridgeman, A., EMBL/GenBank/DDBJ databases (Submitted Apr. 27, 1998). Chromosome 20 Project Group (http://www.sanger.ac.uk/HGP/Chr20/) Sanger Centre.
Lee, N.H., et al., "Rat Genoma Project: Generation of a Rat EST (REST) Catalog & Rat Gene Ind x" Unpublished, (created—Feb. 11, 1998), The Institute for Genomic Research.
NCI-CGAP, "National Cancer Institute, Cancer Genome Anatomy Project (CGAP), Tumor Gene Index http://www.ncbi.nlm.nih.gov/ncicgap" (created—Apr. 26, 1999), Unpublished.

(Continued)

*Primary Examiner*—Tekchand Saidha
*Assistant Examiner*—Christian L. Fronda
(74) *Attorney, Agent, or Firm*—Darby & Darby

(57) ABSTRACT

The present invention relates to a muscle-specific protein, Ozz, and nucleic acids encoding the protein, that regulates development and function of muscle cells. The invention further relates to muscle-specific regulated expression of the protein, and of heterologous genes under control of the same regulatory sequences. In a specific example, a murine Ozz protein of 285 amino acids is preferentially expressed by a 1.0 kb mRNA in heart and skeletal muscle. This protein shares significant homology with neuralized proteins, and associates with a number of muscle proteins, including β-catenin.

11 Claims, 9 Drawing Sheets

OTHER PUBLICATIONS

NCBI GenBank Accession: Q9D0S4 GI:33301416 Definition: Neuralized-like protein 2; 285 aa DBSource: swissprot: locus NRL2_MOUSE, accession Q0D0S4; created: Sep. 15, 2003; sequence updated: Sep. 15, 2003; annotation updated: Sep. 15, 2003.

NCBI GenBank Accession: AK004524 GI:12835749 Definition: Mus musculus 18-day embryo whole body cDNA, RIKEN full-length enriched library, clone:1190009E12 product:hypothetical SOCS domain, C-terminus of STAT-inhibitors containing protein, full insert sequence 1014 bp mRNA linear HTC Sep. 20, 2003.

NCBI GenBank Accession: AL591495 GI:20330140 Definition: Mouse DNA sequence from clone RP23-61O3 on chromosome 2, complete sequence 239758 bp DNA linear ROD Apr. 25, 2002.

NCBI GenBank Accession: NM_080749 GI:18152786 Definition: *Homo sapiens* chromosome 20 open reading frame 163 (C20orf163), mRNA 1269 bp mRNA linear PRI Oct. 5, 2003.

NCBI GenBank Accession: XM_230848 GI:34860696 Definition: *Rattus norvegicus* similar to chromosome 20 open reading frame 163; neuralized-like 2 (LOC311633), mRNA 988 bp mRNA linear ROD Oct. 23, 2003.

* cited by examiner

FIG. 2A

```
   1 CCCTGTTGCA CGGCTTGGAG ATGGCTGCTC CCTCCGAACA CGTAGGACTG
  51 GGTGCCCCAC GGAGCCCTGC GCGCCCAGAG CCCCCTCCCA CCCGCTTCCA
 101 CCAAGTGCAT GGAGCCAACA TCCGCATGGA CCCCTCAGGA ACGCGAGCCA
 151 CACGCGTGGA GAGTTTCGCC CACGGTGTGT GCTTCAGTCG TGAGCCCCTG
 201 GCCCCCGGCC AGGTATTTCT AGTGGAAATT GAGGAAAAAG AGCTGGGCTG
 251 GTGCGGGCAC CTACGTCTTG GCCTGACCGC TCTGGATCCC GCCAGTCTGG
 301 CCGCTGTACC CGAGTTTTCA CTGCCTGACT TGGTCAGCCT TGGCCACAGT
 351 TGGGTCTTCG CTATCACACG CCACCACAAC CGTGTGCCCC GGGAAGGTCA
 401 ACCAGAAGCG GAGGCAGCGG TCCCCAGTGG TCCCCAAGCC CTACTGGTTG
 451 AACCCTATCT GCGCATCGAG CAGTTCCGAA TTCCCCGGGA CCGTCTGGTG
 501 GGCCGCAGCC GGCCAGGGCT TTATAGCCAC CTCTTAGATC AGCTCTATGA
 551 ACAAAACGTG CTGCCTCCTA CAGCGCGCCG AAGCCGCTTG GGTGTTCTCT
 601 TCTGCCCCCG TGAGGATGGG ACCGCCGACA TGCACATCAT CATCAACGGG
 651 GAGGACATGG GCCCTAGCGC CCGGGGGCTG CCAGCTGCTC AGCCCCTCTA
 701 CGCTGTGGTA GATGTGTTTG CTTCCACCAA GAGCGTGCGT CTGGTCCAGC
 751 TGGAGTATGG CTTGCCATCT CTGCAGACTC TGTGCCGACT AGTGATCCAG
 801 AAGAGGGTGG TACACAGGCT GGCCATTGAT GTGCTCCACC TGCCCAAAGG
 851 ACTGAAGGAC TTCTGCAAGT ACGAATGAAC GAATGAACGC CTGTCTGTGG
 901 CCACCAGAGC AAAGTCCCCG GTGGTGCGCC CTGCCTCTAG AGAAGTGGCT
 951 AGTCTGAAGC TGGTCGCACA GCTCACAATC AGGGCTGGAA ATAAATAGAG
1001 CCGATGTGGA TGTTCTGAGA AAAAAAAAAA AAAAAA
```

FIG. 2B

CCTGCCCTAT GGCCGAGAGA TGGCTGCTGC CTCCGAGCCC GTGGATTCGG GTGCACTCTG GGGACTCGAG

CGCCCGGAGC CCCCTCCCAC CCGCTTCCAT CGGGTGCACG GTGCCAACAT CCGCGTGGAC CCCTCTGGGA

CGCGGGCCAC ACGCGTGGAG AGCTTCGCCC ACGGCGTGTG CTTCAGCCGC GAGCCGCTGG CCCCGGGCCA

GGTCTTCCTG GTCGAGATCG AGGAGAAAGA GCTGGGCTGG TGCGGACATC TGCGTCTCGG TCTGACCGCG

CTGGACCCCG CCAGTCTGGC CCCCGTTCCC GAGTTTTCTC TGCCCGATCT GGTCAACCTG GGCCACACCT

GGGTCTTCGC CATCACGCGC CACCACAACC GCGTGCCCCG GGAGGGCCGC CCGGAGGCGG AGGCAGCGGC

CCCCAGCCGA CCTCCAACCC TCCTCGTGGA ACCATATCTG CGCATTGAGC AGTTTCGCAT TCCCCGGGAC

CGCCTGGTGG GCCGCAGCCG GCCAGGGCTC TACAGCCATC TCTTGGACCA GCTCTATGAG CTGAACGTGC

TGCCTCCGAC CGCGCGCCGT AGCCGCCTGG GTGTCCTCTT TTGCCCGCGC CCCGATGGCA CGGCCGACAT

GCACATCATC ATCAACGGCG AGGACATGGG CCCGAGCGCC CGGGGACTGC CAGCTGCGCA GCCCCTCTAC

GCGGTGGTGG ACGTGTTTGC TTCCACAAAG AGCGTGCGCC TTGTCCAGCT CGAGTATGGC TTGCCATCCC

TGCAGACTCT GTGCCGCCTA GTGATACAAA GGAGCATGGT GCACCGGCTG GCCATTGATG GGCTCCACCT

GCCCAAAGAA CTTAAGGATT TCTGCAAGTA TGAGTGAAGA CCCACAGTGC ACCAGAGCAC AGCTGCATCC

TGGAGCCCCA GACCTGTGGC TGGCTGGTCC GAAGTTGGCC ACATTGCTGC CAGCCAAGAC

FIG. 4

SOCS-box (P/hxS/T/PLQH/YhCRxxhxxxhx2-10hxxLPhPxxhxY/FLx1-3Y/F)

Casein kinase II-phosphorylation site

Tyrosine kinase-phosphorylation site

Protein kinase C-phosphorylation site

BC-box (T/SL/MxxxC/SxxxV/L/I)

```
human:   1  MAAASEPVDSGALWGLERPEPPPTRFHRVHGANIRVDPSGTRATRVESFAHGVCFSREPL  60
            MAA SE V  GA      RPEPPPTRFH+VHGANIR+DPSGTRATRVESFAHGVCFSREPL
mouse:   1  MAAPSEHVGLGAPRSPARPEPPPTRFHQVHGANIRMDPSGTRATRVESFAHGVCFSREPL  60

human:  61  APGQVFLVEIEEKELGWCGHLRLGLTALDPASLAPVPEFSLPDLVNLGHTWVFAITRHHN 120
            APGQVFLVEIEEKELGWCGHLRLGLTALDPASLA VPEFSLPDLV+LGH+WVFAITRHHN
mouse:  61  APGQVFLVEIEEKELGWCGHLRLGLTALDPASLAAVPEFSLPDLVSLGHSWVFAITRHHN 120

human: 121  RVPREGRPEAEAAAPSRPPTLLVEPYLRIEQFRIPRDRLVGRSRPGLYSHLLDQLYELNV 180
            RVPREG+PEAEAA PS P  LLVEPYLRIEQFRIPRDRLVGRSRPGLYSHLLDQLYE NV
mouse: 121  RVPREGQPEAEAAVPSGPQALLVEPYLRIEQFRIPRDRLVGRSRPGLYSHLLDQLYEQNV 180

human: 181  LPPTARRSRLGVLFCPRPDGTADMHIIINGEDMGPSARGLPAAQPLYAVVDVFASTKSVR 240
            LPPTARRSRLGVLFCPR DGTADMHIIINGEDMGPSARGLPAAQPLYAVVDVFASTKSVR
mouse: 181  LPPTARRSRLGVLFCPREDGTADMHIIINGEDMGPSARGLPAAQPLYAVVDVFASTKSVR 240

human: 241  LVQLEYGLPSLQTLCRLVIQRSMVHRLAIDGLHLPKFLKDFCKYE 285
            LVQLEYGLPSLQTLCRLVIQ+ +VHRLAID LHLPK LKDFCKYE
mouse: 241  LVQLEYGLPSLQTLCRLVIQKRVVHRLAIDVLHLPKGLKDFCKYE 285
```

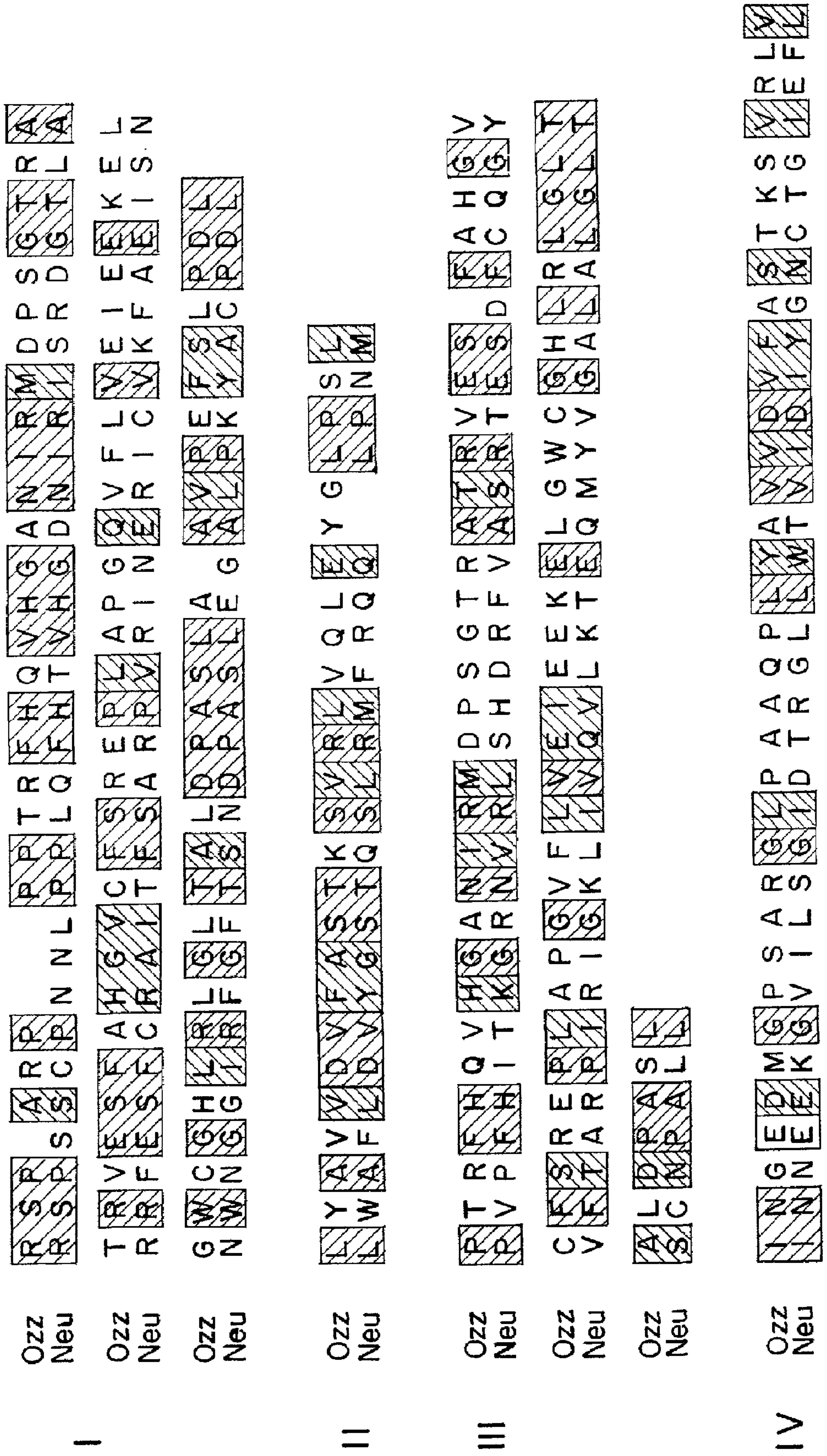

FIG. 6

I
Ozz  RSPARPPTRFHQVHGANIRMDPSGTRA
Neu  RSPSSCRNNLPRLQFHTVHGDNLRSRDGTLA

Ozz  TRVESFAHGVCFSREPLAPGQVFLVEIEKEL
Neu  RRFESCRATESARPVRINERICVKFAEISN

Ozz  GWCGHLRLGLTALDPASLAAVPEFSLPDL
Neu  NWNGGLRFGFTSNDPASLEGALPKYACPDL

II
Ozz  LYAVDVFASTKSVRLVQLEYGLPSL
Neu  WAFLDVYGSTQSLRMFRQLPNM

III
Ozz  PTRFHQVHGANIRMDPSGTRATRVESFAHGV
Neu  RVPFHITKGRNVRLSHDRFVASRTESDFCQGY

Ozz  CFSREPLAPGQVFLVEIEKELGWCGHRLGLT
Neu  VFTARPIRIGKLIVQVLKTEQMYVGAALGLT

Ozz  ALDPASLA
Neu  SCNPASLT

IV
Ozz  INGEDMGPSARGLPAAQPLYAVDVFASTKSVRLL
Neu  NNEEKGVILSGHDTRGLLWTVDIYGNCTGEFL

FIG. 7
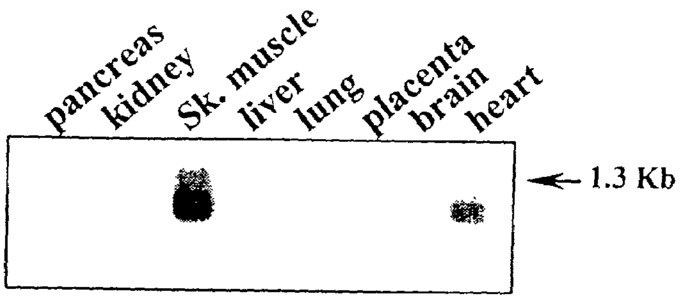
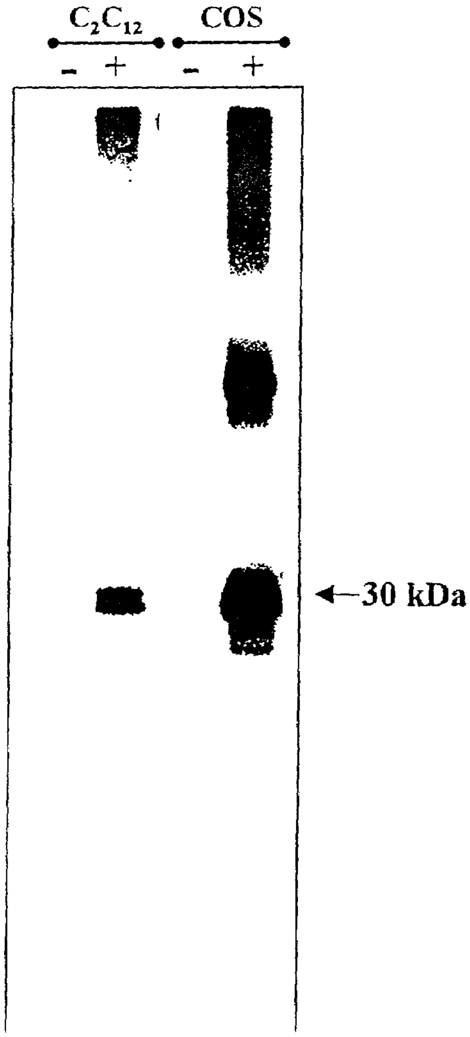
FIG. 8

SEQUENCE LISTING

```
<160> NUMBER OF SEQ ID NOS: 24

<210> SEQ ID NO 1
<211> LENGTH: 1036
<212> TYPE: DNA
<213> ORGANISM: Mus musculus

<400> SEQUENCE: 1

ccctgttgca cggcttggag atggctgctc cctccgaaca cgtaggactg ggtgccccac     60

ggagccctgc gcgcccagag ccccctccca cccgcttcca ccaagtgcat ggagccaaca    120

tccgcatgga cccctcagga acgcgagcca cacgcgtgga gagtttcgcc cacggtgtgt    180

gcttcagtcg tgagcccctg gcccccggcc aggtatttct agtggaaatt gaggaaaaag    240

agctgggctg gtgcgggcac ctacgtcttg gcctgaccgc tctggatccc gccagtctgg    300

ccgctgtacc cgagttttca ctgcctgact tggtcagcct tggccacagt tgggtcttcg    360

ctatcacacg ccaccacaac cgtgtgcccc gggaaggtca accagaagcg gaggcagcgg    420

tccccagtgg tccccaagcc ctactggttg aaccctatct gcgcatcgag cagttccgaa    480

ttccccggga ccgtctggtg ggccgcagcc ggccagggct ttatagccac ctcttagatc    540

agctctatga acaaaacgtg ctgcctccta cagcgcgccg aagccgcttg ggtgttctct    600

tctgcccccg tgaggatggg accgccgaca tgcacatcat catcaacggg gaggacatgg    660

gccctagcgc ccgggggctg ccagctgctc agcccctcta cgctgtggta gatgtgtttg    720

cttccaccaa gagcgtgcgt ctggtccagc tggagtatgg cttgccatct ctgcagactc    780

tgtgccgact agtgatccag aagagggtgg tacacaggct ggccattgat gtgctccacc    840

tgcccaaagg actgaaggac ttctgcaagt acgaatgaac gaatgaacgc ctgtctgtgg    900
```

-continued

```
ccaccagagc aaagtccccg gtggtgcgcc ctgcctctag agaagtggct agtctgaagc    960

tggtcgcaca gctcacaatc agggctggaa ataaatagag ccgatgtgga tgttctgaga   1020

aaaaaaaaaa aaaaaa                                                   1036


<210> SEQ ID NO 2
<211> LENGTH: 285
<212> TYPE: PRT
<213> ORGANISM: Mus musculus

<400> SEQUENCE: 2

Met Ala Ala Pro Ser Glu His Val Gly Leu Gly Ala Pro Arg Ser Pro
 1               5                  10                  15

Ala Arg Pro Glu Pro Pro Pro Thr Arg Phe His Gln Val His Gly Ala
            20                  25                  30

Asn Ile Arg Met Asp Pro Ser Gly Thr Arg Ala Thr Arg Val Glu Ser
        35                  40                  45

Phe Ala His Gly Val Cys Phe Ser Arg Glu Pro Leu Ala Pro Gly Gln
    50                  55                  60

Val Phe Leu Val Glu Ile Glu Glu Lys Glu Leu Gly Trp Cys Gly His
65                  70                  75                  80

Leu Arg Leu Gly Leu Thr Ala Leu Asp Pro Ala Ser Leu Ala Ala Val
                85                  90                  95

Pro Glu Phe Ser Leu Pro Asp Leu Val Ser Leu Gly His Ser Trp Val
            100                 105                 110

Phe Ala Ile Thr Arg His His Asn Arg Val Pro Arg Glu Gly Gln Pro
        115                 120                 125

Glu Ala Glu Ala Ala Val Pro Ser Gly Pro Gln Ala Leu Leu Val Glu
    130                 135                 140

Pro Tyr Leu Arg Ile Glu Gln Phe Arg Ile Pro Arg Asp Arg Leu Val
145                 150                 155                 160

Gly Arg Ser Arg Pro Gly Leu Tyr Ser His Leu Leu Asp Gln Leu Tyr
                165                 170                 175

Glu Gln Asn Val Leu Pro Pro Thr Ala Arg Arg Ser Arg Leu Gly Val
            180                 185                 190

Leu Phe Cys Pro Arg Glu Asp Gly Thr Ala Asp Met His Ile Ile Ile
        195                 200                 205

Asn Gly Glu Asp Met Gly Pro Ser Ala Arg Gly Leu Pro Ala Ala Gln
    210                 215                 220

Pro Leu Tyr Ala Val Val Asp Val Phe Ala Ser Thr Lys Ser Val Arg
225                 230                 235                 240

Leu Val Gln Leu Glu Tyr Gly Leu Pro Ser Leu Gln Thr Leu Cys Arg
                245                 250                 255

Leu Val Ile Gln Lys Arg Val Val His Arg Leu Ala Ile Asp Val Leu
            260                 265                 270

His Leu Pro Lys Gly Leu Lys Asp Phe Cys Lys Tyr Glu
        275                 280                 285


<210> SEQ ID NO 3
<211> LENGTH: 970
<212> TYPE: DNA
<213> ORGANISM: Homo sapiens

<400> SEQUENCE: 3

cctgccctat ggccgagaga tggctgctgc ctccgagccc gtggattcgg gtgcactctg     60
```

-continued

```
gggactcgag cgcccggagc cccctcccac ccgcttccat cgggtgcacg gtgccaacat    120

ccgcgtggac ccctctggga cgcgggccac acgcgtggag agcttcgccc acggcgtgtg    180

cttcagccgc gagccgctgg ccccgggcca ggtcttcctg gtcgagatcg aggagaaaga    240

gctgggctgg tgcggacatc tgcgtctcgg tctgaccgcg ctggaccccg ccagtctggc    300

ccccgttccc gagttttctc tgcccgatct ggtcaacctg ggccacacct gggtcttcgc    360

catcacgcgc caccacaacc gcgtgccccg ggagggccgc ccggaggcgg aggcagcggc    420

ccccagccga cctccaaccc tcctcgtgga accatatctg cgcattgagc agtttcgcat    480

tccccgggac cgcctggtgg gccgcagccg gccagggctc tacagccatc tcttggacca    540

gctctatgag ctgaacgtgc tgcctccgac cgcgcgccgt agccgcctgg gtgtcctctt    600

ttgcccgcgc cccgatggca cggccgacat gcacatcatc atcaacggcg aggacatggg    660

cccgagcgcc cggggactgc cagctgcgca gcccctctac gcggtggtgg acgtgtttgc    720

ttccacaaag agcgtgcgcc ttgtccagct cgagtatggc ttgccatccc tgcagactct    780

gtgccgccta gtgatacaaa ggagcatggt gcaccggctg gccattgatg ggctccacct    840

gcccaaagaa cttaaggatt tctgcaagta tgagtgaaga cccacagtgc accagagcac    900

agctgcatcc tggagcccca gacctgtggc tggctggtcc gaagttggcc acattgctgc    960

cagccaagac                                                           970
```

```
<210> SEQ ID NO 4
<211> LENGTH: 285
<212> TYPE: PRT
<213> ORGANISM: Homo sapiens

<400> SEQUENCE: 4

Met Ala Ala Ala Ser Glu Pro Val Asp Ser Gly Ala Leu Trp Gly Leu
 1               5                  10                  15

Glu Arg Pro Glu Pro Pro Pro Thr Arg Phe His Arg Val His Gly Ala
            20                  25                  30

Asn Ile Arg Val Asp Pro Ser Gly Thr Arg Ala Thr Arg Val Glu Ser
        35                  40                  45

Phe Ala His Gly Val Cys Phe Ser Arg Glu Pro Leu Ala Pro Gly Gln
    50                  55                  60

Val Phe Leu Val Glu Ile Glu Glu Lys Glu Leu Gly Trp Cys Gly His
65                  70                  75                  80

Leu Arg Leu Gly Leu Thr Ala Leu Asp Pro Ala Ser Leu Ala Pro Val
                85                  90                  95

Pro Glu Phe Ser Leu Pro Asp Leu Val Asn Leu Gly His Thr Trp Val
            100                 105                 110

Phe Ala Ile Thr Arg His His Asn Arg Val Pro Arg Glu Gly Arg Pro
        115                 120                 125

Glu Ala Glu Ala Ala Ala Pro Ser Arg Pro Pro Thr Leu Leu Val Glu
    130                 135                 140

Pro Tyr Leu Arg Ile Glu Gln Phe Arg Ile Pro Arg Asp Arg Leu Val
145                 150                 155                 160

Gly Arg Ser Arg Pro Gly Leu Tyr Ser His Leu Leu Asp Gln Leu Tyr
                165                 170                 175

Glu Leu Asn Val Leu Pro Pro Thr Ala Arg Arg Ser Arg Leu Gly Val
            180                 185                 190

Leu Phe Cys Pro Arg Pro Asp Gly Thr Ala Asp Met His Ile Ile Ile
        195                 200                 205
```

-continued

```
Asn Gly Glu Asp Met Gly Pro Ser Ala Arg Gly Leu Pro Ala Ala Gln
    210                 215                 220

Pro Leu Tyr Ala Val Val Asp Val Phe Ala Ser Thr Lys Ser Val Arg
225                 230                 235                 240

Leu Val Gln Leu Glu Tyr Gly Leu Pro Ser Leu Gln Thr Leu Cys Arg
                245                 250                 255

Leu Val Ile Gln Arg Ser Met Val His Arg Leu Ala Ile Asp Gly Leu
            260                 265                 270

His Leu Pro Lys Glu Leu Lys Asp Phe Cys Lys Tyr Glu
        275                 280                 285


<210> SEQ ID NO 5
<211> LENGTH: 91
<212> TYPE: PRT
<213> ORGANISM: Mus musculus

<400> SEQUENCE: 5

Arg Ser Pro Ala Arg Pro Glu Pro Pro Pro Thr Arg Phe His Gln Val
 1               5                  10                  15

His Gly Ala Asn Ile Arg Met Asp Pro Ser Gly Thr Arg Ala Thr Arg
            20                  25                  30

Val Glu Ser Phe Ala His Gly Val Cys Phe Ser Arg Glu Pro Leu Ala
        35                  40                  45

Pro Gly Gln Val Phe Leu Val Glu Ile Glu Glu Lys Glu Leu Gly Trp
    50                  55                  60

Cys Gly His Leu Arg Leu Gly Leu Thr Ala Leu Asp Pro Ala Ser Leu
65                  70                  75                  80

Ala Ala Val Pro Glu Phe Ser Leu Pro Asp Leu
                85                  90


<210> SEQ ID NO 6
<211> LENGTH: 94
<212> TYPE: PRT
<213> ORGANISM: Drosophila virilis

<400> SEQUENCE: 6

Arg Ser Pro Ser Ser Cys Pro Asn Asn Leu Pro Pro Leu Gln Phe His
 1               5                  10                  15

Thr Val His Gly Asp Asn Ile Arg Ile Ser Arg Asp Gly Thr Leu Ala
            20                  25                  30

Arg Arg Phe Glu Ser Phe Cys Arg Ala Ile Thr Phe Ser Ala Arg Pro
        35                  40                  45

Val Arg Ile Asn Glu Arg Ile Cys Val Lys Phe Ala Glu Ile Ser Asn
    50                  55                  60

Asn Trp Asn Gly Gly Ile Arg Phe Gly Phe Thr Ser Asn Asp Pro Ala
65                  70                  75                  80

Ser Leu Glu Gly Ala Leu Pro Lys Tyr Ala Cys Pro Asp Leu
                85                  90


<210> SEQ ID NO 7
<211> LENGTH: 26
<212> TYPE: PRT
<213> ORGANISM: Mus musculus

<400> SEQUENCE: 7

Leu Tyr Ala Val Val Asp Val Phe Ala Ser Thr Lys Ser Val Arg Leu
 1               5                  10                  15

Val Gln Leu Glu Tyr Gly Leu Pro Ser Leu
```

-continued

```
        20                  25


<210> SEQ ID NO 8
<211> LENGTH: 24
<212> TYPE: PRT
<213> ORGANISM: Drosophila virilis

<400> SEQUENCE: 8

Leu Trp Ala Phe Leu Asp Val Tyr Gly Ser Thr Gln Ser Leu Arg Met
 1               5                  10                  15

Phe Arg Gln Gln Leu Pro Asn Met
            20


<210> SEQ ID NO 9
<211> LENGTH: 71
<212> TYPE: PRT
<213> ORGANISM: Mus musculus

<400> SEQUENCE: 9

Pro Thr Arg Phe His Gln Val His Gly Ala Asn Ile Arg Met Asp Pro
 1               5                  10                  15

Ser Gly Thr Arg Ala Thr Arg Val Glu Ser Phe Ala His Gly Val Cys
            20                  25                  30

Phe Ser Arg Glu Pro Leu Ala Pro Gly Gln Val Phe Leu Val Glu Ile
        35                  40                  45

Glu Glu Lys Glu Leu Gly Trp Cys Gly His Leu Arg Leu Gly Leu Thr
    50                  55                  60

Ala Leu Asp Pro Ala Ser Leu
65                  70


<210> SEQ ID NO 10
<211> LENGTH: 71
<212> TYPE: PRT
<213> ORGANISM: Drosophila virilis

<400> SEQUENCE: 10

Pro Val Pro Phe His Ile Thr Lys Gly Arg Asn Val Arg Leu Ser His
 1               5                  10                  15

Asp Arg Phe Val Ala Ser Arg Thr Glu Ser Asp Phe Cys Gln Gly Tyr
            20                  25                  30

Val Phe Thr Ala Arg Pro Ile Arg Ile Gly Lys Leu Ile Val Gln Val
        35                  40                  45

Leu Lys Thr Glu Gln Met Tyr Val Gly Ala Leu Ala Leu Gly Leu Thr
    50                  55                  60

Ser Cys Asn Pro Ala Leu Leu
65                  70


<210> SEQ ID NO 11
<211> LENGTH: 35
<212> TYPE: PRT
<213> ORGANISM: Mus musculus

<400> SEQUENCE: 11

Ile Asn Gly Glu Asp Met Gly Pro Ser Ala Arg Gly Leu Pro Ala Ala
 1               5                  10                  15

Gln Pro Leu Tyr Ala Val Val Asp Val Phe Ala Ser Thr Lys Ser Val
            20                  25                  30

Arg Leu Val
        35
```

-continued

<210> SEQ ID NO 12
<211> LENGTH: 35
<212> TYPE: PRT
<213> ORGANISM: Drosophila virilis

<400> SEQUENCE: 12

```
Ile Asn Asn Glu Glu Lys Gly Val Ile Leu Ser Gly Ile Asp Thr Arg
 1               5                  10                  15

Gly Leu Leu Trp Thr Val Ile Asp Ile Tyr Gly Asn Cys Thr Gly Ile
            20                  25                  30

Glu Phe Leu
        35
```

<210> SEQ ID NO 13
<211> LENGTH: 494
<212> TYPE: DNA
<213> ORGANISM: Homo sapiens

<400> SEQUENCE: 13

```
agccatactc gagctggaca aggcgcacgc tctttgtgga agcaaacacg tccaccaccg     60

cgtagagggg ctgcgcagct ggcagtcccc gggcgctcgg gcccatgtcc tcgccgttga    120

tgatgatgtg catgtcggcc gtgccatcgg ggcgcgggca aaagaggaca cccaggcggc    180

tacggcgcgc ggtcggaggc agcacgttca gctcatagag ctggtccaag agatggctgt    240

agagccctgc cgctgcggcc caccaggcgg tcccggggaa tgcgaaactg ctcaatgcgc    300

agatatggtt ccacgaggag ggttggaggt cggctggggg ccgctgcctg cctccgggcg    360

gcctcccggg gcacgcggtt gtggtggcgc gtgatggcga agacccaggt gtggcccagg    420

ttgaccaaga tcgggcagag aaaactcggg aacgggggcc agactggcgg ggtccagcgc    480

ggtcagaccg agac                                                      494
```

<210> SEQ ID NO 14
<211> LENGTH: 499
<212> TYPE: DNA
<213> ORGANISM: Mus musculus

<400> SEQUENCE: 14

```
agccatactc cagctggacc agacgccacg ctcttggtgg aagcaaacac atctaccaca     60

gcgtagaggg gctgagcagc tggcagcccc cgggcgctag ggcccatgtc ctccccgttg    120

atgatgatgt gcatgtcggc ggtcccatcc tcacgggggc agaagagaac acccaagcgg    180

cttcggcgcg ctgtaggagg cagcacgttt tgttcataga gctgatctaa gaggtggcta    240

taaagccctg gccggctgcg gcccaccaga cggtcccggg gaattcggaa ctgctcgatg    300

cgcagatagg gttcaaccag tagggcttgg ggaccactgg ggaccgctgc ctccgcttct    360

ggttgacctt cccggggcac acggttgtgg tggcgtgtga tagcgaagac ccaactgtgg    420

ccaaggctga ccaagtcagg cagtgaaaac tcgggtacag cggccagact ggcgggatcc    480

agagcggtca ggccaagac                                                 499
```

<210> SEQ ID NO 15
<211> LENGTH: 367
<212> TYPE: DNA
<213> ORGANISM: Homo sapiens

<400> SEQUENCE: 15

```
agctggcgcc gggggctatt ttgggcggcg ggcaatgatg gtgaccgcaa ggcgaccttg     60
```

-continued taaggcattt ccccctgac tcccttcccc gagcctctgc ccgggggtcc tagcgccgct 120
ttctcagcca tcccgcctac aacttagccg tccacaacag gatcatctga tcgcgtgcgc 180
ccgggctacg atctgcgagg cccgcggacc ttgacccggc attgaccgcc accgcccccc 240
aggtccgtag ggaccaaaga aggggcggga ggaagactgt cacgtggcgc cggagttcac 300
gtgactcgta cacatgactt ccagtccccg ggcgcctcct ggagagcaag gacgcggggg 360
agcagag 367

<210> SEQ ID NO 16
<211> LENGTH: 367
<212> TYPE: DNA
<213> ORGANISM: Homo sapiens

<400> SEQUENCE: 16
agctggcgcc gggggctatt ttgggcggcg ggcaatgatg gtgaccgcaa ggcgaccttg 60
taaggcattt ccccctgac tcccttcccc gagcctctgc ccgggggtcc tagcgccgct 120
ttctcagcca tcccgcctac aacttagccg tccacaacag gatcatctga tcgcgtgcgc 180
ccgggctacg atctgcgagg cccgcggacc ttgacccggc attgaccgcc accgcccccc 240
aggtccgtag ggaccaaaga aggggcggga ggaagactgt cacgtggcgc cggagttcac 300
gtgactcgta cacatgactt ccagtccccg ggcgcctcct ggagagcaag gacgcggggg 360
agcagag 367

<210> SEQ ID NO 17
<211> LENGTH: 387
<212> TYPE: DNA
<213> ORGANISM: Mus musculus

<400> SEQUENCE: 17
agctcatgcc aagggctatt ttgggcagcg ggctcagatt gtgacgcggg ggcgggtgga 60
tgaaccatgt aaggcatttc cccttctct aacttccccc agctctgcct gggggtccta 120
gcgccgcttt ctcgcttgtc accagtaagg ggtccccagg agcctgggga acccttctgt 180
caacaccaag atcacctgat ctctggcacc ctgactaata accttcaggg ccacgcactt 240
tgaccactcc cgaccctcag gcccacagat taaaaaagtg aacaatgagc aaactgtcac 300
gtgatgcaga tgctcacgtg accagagcta cacatgactt ccagtccaaa ggcgcctcct 360
ggagagcaag gacgcaagga agcagag 387

<210> SEQ ID NO 18
<211> LENGTH: 387
<212> TYPE: DNA
<213> ORGANISM: Mus musculus

<400> SEQUENCE: 18
agctcatgcc aagggctatt ttgggcagcg ggctcagatt gtgacgcggg ggcgggtgga 60
tgaaccatgt aaggcatttc cccttctct aacttccccc agctctgcct gggggtccta 120
gcgccgcttt ctcgcttgtc accagtaagg ggtccccagg agcctgggga acccttctgt 180
caacaccaag atcacctgat ctctggcacc ctgactaata accttcaggg ccacgcactt 240
tgaccactcc cgaccctcag gcccacagat taaaaaagtg aacaatgagc aaactgtcac 300
gtgatgcaga tgctcacgtg accagagcta cacatgactt ccagtccaaa ggcgcctcct 360
ggagagcaag gacgcaagga agcagag 387

-continued

<210> SEQ ID NO 19
<211> LENGTH: 6
<212> TYPE: PRT
<213> ORGANISM: Homo sapiens

<400> SEQUENCE: 19

```
Gly Thr Arg Ala Thr Arg
 1              5
```

<210> SEQ ID NO 20
<211> LENGTH: 6
<212> TYPE: PRT
<213> ORGANISM: Homo sapiens

<400> SEQUENCE: 20

```
Gly Val Cys Phe Ser Arg
 1              5
```

<210> SEQ ID NO 21
<211> LENGTH: 5
<212> TYPE: PRT
<213> ORGANISM: Homo sapiens

<400> SEQUENCE: 21

```
Gly Gln Pro Glu Ala
 1              5
```

<210> SEQ ID NO 22
<211> LENGTH: 9
<212> TYPE: PRT
<213> ORGANISM: Homo sapiens

<400> SEQUENCE: 22

```
Lys Gly Leu Lys Asp Phe Cys Lys Tyr
 1              5
```

<210> SEQ ID NO 23
<211> LENGTH: 37
<212> TYPE: PRT
<213> ORGANISM: Homo sapiens

<400> SEQUENCE: 23

```
Pro Ser Leu Gln Thr Leu Cys Arg Leu Val Ile Gln Arg Ser Met Val
 1              5                   10                  15

His Arg Leu Ala Ile Asp Gly Leu His Leu Pro Lys Glu Leu Lys Asp
            20                  25                  30

Phe Cys Lys Tyr Glu
        35
```

<210> SEQ ID NO 24
<211> LENGTH: 10
<212> TYPE: PRT
<213> ORGANISM: Unknown
<220> FEATURE:
<223> OTHER INFORMATION: BC box consensus sequence: Ser can be either Ser or Thr, followed by Leu or Met, followed by any 3 amino acids, followed by Cys or Ser, followed by any 3 amino acids, followed by Val, Ile, or Leu

<400> SEQUENCE: 24

```
Ser Leu Xaa Xaa Xaa Cys Xaa Xaa Xaa Ile
 1              5                   10
```

PROTEIN SPECIFIC FOR CARDIAC AND SKELETAL MUSCLE

CROSS-REFERENCE TO RELATED APPLICATION

This is a continuation of international application Serial No. PCT/US00/11900, filed Apr. 28, 2000, the entire disclosure of which is hereby incorporated by reference.

This application claims priority under 35 U.S.C. §119 based upon U.S. Provisional Application Ser. No. 60/131,814 filed Apr. 29, 1999, the entire disclosure of which is incorporated herein by reference.

FIELD OF THE INVENTION

The present invention relates to a muscle-specific protein, and nucleic acids encoding the protein, that regulates development and function of muscle cells. Tie invention further relates to muscle-specific regulated expression of the protein, and of heterologous genes under control of the same regulatory sequences

BACKGROUND OF THE INVENTION

The human and mouse protective protein/cathepsin A (PPCA) genes are highly homologous, both in sequence and organization. Their expression in mammalian tissues is ubiquitous but differential. The mouse gene is transcribed from two promoters, giving rise to two mRNAs which differ in size and tissue distribution. The less abundant, larger transcript of 2.0 kb is present only in a few tissues and is transcribed from a tissue-specific promoter, upstream of the constitutive promoter present in both the human and mouse genes. Northern blot hybridizations demonstrated that these two mRNAs differed only in their 5'UTRs.

PPCA is a lysosomal carboxypeptidase that is deficient in the human lysosomal storage disease galactosialidosis (reviewed in d'Azzo et al., In *The Metabolic and Molecular Bases of Inherited Disease*, C. Scriver et al. (eds.), New York: McGraw-Hill Publishing Co., pp. 2825–38, 1995). The human and mouse PPCA cDNAs are 85% homologous in their coding regions and 72% identical in the 3' untranslated regions (Galjart, et al., Cell, 54:755–764, 1988; Galjart, et al., J. Biol. Chem., 265:4678–84, 1990). The genomic organization and structure of the two PPCA genes are also conserved. The human gene maps to chromosome 20q13.1 and the mouse to the syntenic region of chromosome 2-H4 (Wiegant, et al., Genomics, 10:345–349, 1991; Williamson, et al., Genomics, 22:240–242, 1994; Shimmoto, et al., Biochem. Biophys. Res. Comm., 220:802–806, 1996; Rottier and d'Azzo, DNA Cell Biol., 16:599–610, 1997). Shimmoto, et al. showed that the last exon of the human gene, exon XV, partially overlaps over a stretch of 58 nucleotides (nt) with the gene encoding the phospholipid transfer protein (PLTP; Shimmoto, et al., supra). Similarly, the murine PPCA and PLTP genes are in close vicinity and probably overlap as well. Whether these two genes share common regulatory elements is unknown at the moment.

SUMMARY OF THE INVENTION

The present invention provides a novel protein, termed Ozz, which is involved in development and function of muscle. Thus, in one aspect, an isolated and, preferably, purified, Ozz protein is provided. In specific embodiments, the protein is a human Ozz or a murine Ozz.

Also provided are fragments, analogs, and derivatives of Ozz, which are characterized by the ability to bind a protein selected from the group consisting of β-catenin, myosin, c-Nap, and Alix.

In a further embodiment, a polypeptide fragment of Ozz protein is provided. The fragment of Ozz may have a property of about 40% sequence identity to a duplicated neuralized homology repeat of neuralized protein of Drosphila; or a polypeptide comprising a stretch of about 30 amino acids at the C-terminus homologous to two regions of neutralized proteins; or a peptide comprising an amino acid sequence selected form the group consisting of GTRATR (SEQ ID NO:19), GVCFSR (SEQ ID NO:20), GQPEA (SEQ ID NO:21), and KGLKDFCKY (SEQ ID NO:22); or specific binding activity with an anti-Ozz antibody.

The invention further provides an isolated oligonucleotide encoding Ozz protein. Further provided is a vector comprising a nucleic acid encoding a polypeptide fragment of Ozz, including full length Ozz, operatively associated with an expression control sequence, wherein the polypeptide has the ability to bind a β-catenin, myosin, c-Nap, or Alix protein, as well as a cell comprising such a vector, or a non-human animal transformed with such a vector.

In a further embodiment, the invention provides an isolated nucleic acid of at least ten bases, preferably of at least about 17 to about 20 bases, that hybridizes under stringent conditions with a nucleic acid having a nucleotide sequence as depicted in SEQ ID NO:1 or 3, with the proviso that the nucleic acid is not a PPCA exon I.

The invention further provides an Ozz muscle-specific promoter, which provides for targeted, tissue-specific expression.

A further aspect of the invention relates to an antibody that specifically binds to Ozz protein, and related methods for detecting an Ozz protein comprising detecting binding of the antibody to a protein in a sample suspected of containing an Ozz protein.

Alternatively, expression of Ozz can be detected by detecting mRNA encoding Ozz in a sample from a cell suspected of expressing Ozz.

In a further embodiment, the discovery of Ozz provides a method for detecting damage to muscle tissue comprising detecting an increase in the level of Ozz protein in a blood or a blood fraction, wherein the presence of an increase in the level of Ozz in blood or a blood fraction indicates damage to muscle tissue.

Another embodiment of the invention relates to a method of detecting a disease associated with a defect in Ozz expression comprising detecting an abnormal amount or localization pattern of Ozz in muscle cells from a subject.

These and further aspects of the invention are more fully disclosed in the drawings, description, and examples below.

BRIEF DESCRIPTION OF THE DRAWINGS

FIGS. 2A and B. (A) Murine Ozz cDNA sequence (SEQ ID NO:1) and (B) human Ozz cDNA sequence (SEQ ID NO:3). The ATG translation start site and TGA termination site are indicated with bold text.

FIG. 4. Amino acid sequence of mouse Ozz protein (SEQ ID NO:2) and human Ozz protein (SEQ ID NO:4). Putative phosphorylation sites for casein II (T44, T86, and S100; light shading), protein kinase C (T184, S216, S235, and S238; dark shading), and tyrosine kinase (Y284; medium shading); and SOCS box (residues 249–285; darker shading), and BC box (residues 250–259; lighter shading) consensus domains are shown.

FIG. 6. Sequence alignment between Ozz protein (SEQ ID NOS:5, 7, 9, and 11) and *D. virilis* neuralized protein (SEQ ID NOS:6, 8, 10, and 12).

FIG. 7. Immunoprecipitation of Ozz protein in $C_2C_{12}$ and COS transfected cells, using anti-Ozz antibodies.

FIG. 8. Human multi-tissue Northern blot using full-length mouse Ozz cDNA as a probe.

DETAILED DESCRIPTION OF THE INVENTION

Figure 1:
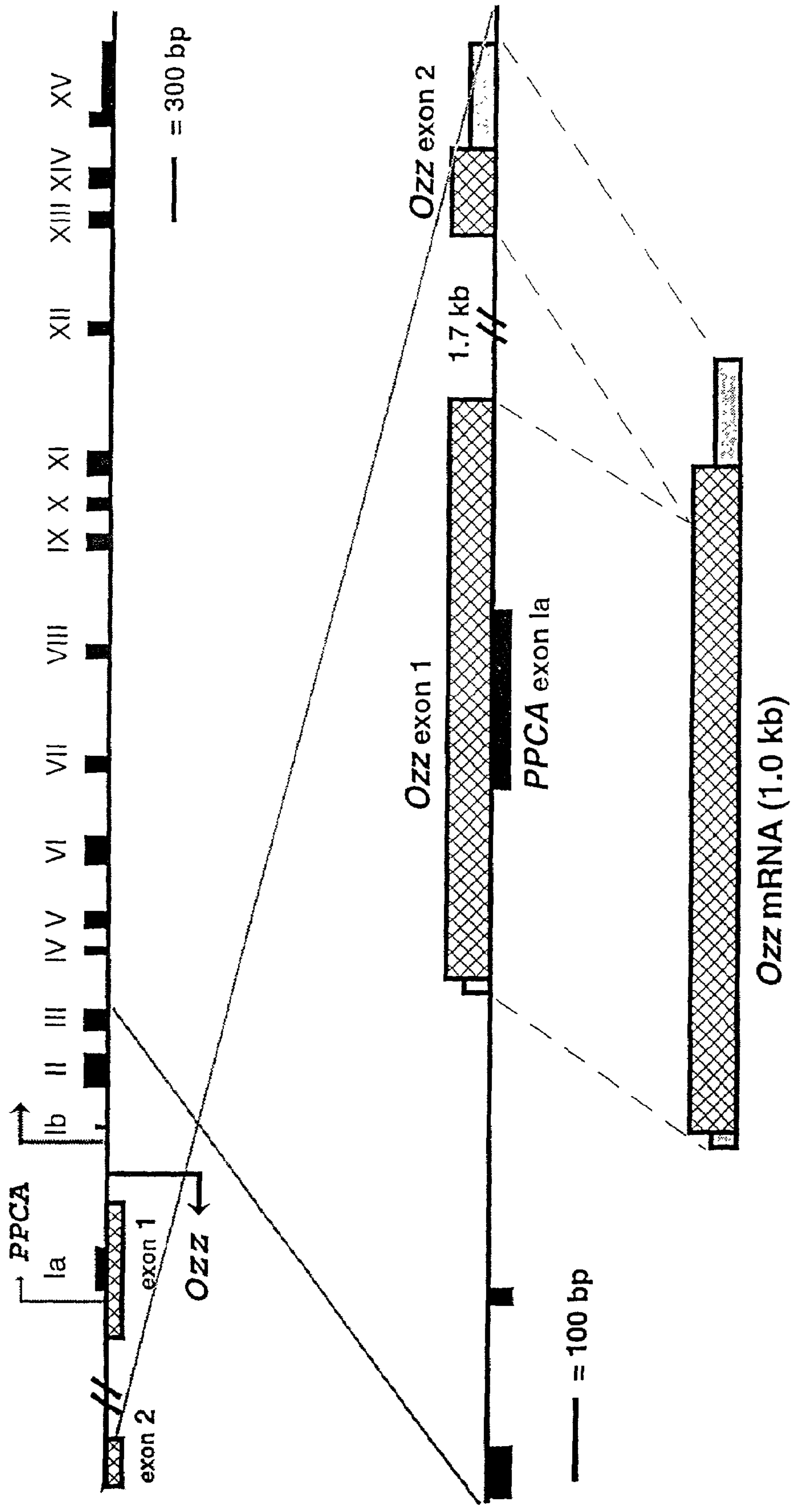
FIG. 1. Schematic drawing of genetic structure of the PPCA and Ozz genes. The Ozz gene is enlarged; the mRNA structure is shown below it.

Analysis of the 5' regions of the human and mouse PPCA genes led to the identification of their minimal promoter, which bears characteristics of housekeeping gene promoters and drives the transcription of an ubiquitously expressed mRNA. In addition, an alternative upstream promoter, present only in the mouse gene, that controls expression of a larger transcript of 2 kb present only in some tissues was found (Rottier and d'Azzo, DNA Cell Biol., 16:599–610, 1997). Functional analysis of the second PPCA transcript in mouse tissues brought the discovery of a new transcriptional unit, overlapping with exon Ia of the mouse PPCA gene. Thus, the present invention is based, in part, on the isolation and characterization of the corresponding cDNA and encoded protein, which has been named Ozz.

The primary structure of Ozz shows homology to the product of a developmental gene of *Drosophila*, called neuralized (neu), also found in *C. elegans* and humans. The *Drosophila neu* is a member of the neurogenic gene family that determine the cell fate in the developing central nervous system of the fly embryo (Corbin, et al., Cell, 67:311–23, 1991; Martin-Bermundo, et al., Development, 121:219–24, 1995; Hartenstein, et al., Development, 116:203–20, 1992). Absence of neu in the embryo results in an excess of neuroblasts, suggesting that neuralized plays a role in determining cell fate in the neurogenic region of the embryo. The neuralized protein contains four domains: a nuclear localization signal, a homeodomain similarity, a helix-turn-helix motif, a zinc-finger region, as well as a potential DNA binding domain, the RING zinc-finger domain (Price, et al., EMBO J., 12:2411–18, 1993). In addition, neuralized includes a stretch of 100 amino acids which is repeated twice in the *Drosophila*, human and *C. elegans* proteins, and is called NHR (Neuralized Homologous Region) (Nakamura, et al., Oncogene, 16:1009–19, 1998). The NHR domain is present in the N-terminal region of the Ozz protein. Ozz mRNA and protein are preferentially expressed in embryonal and adult muscle tissues. Ozz is likely to be involved in muscle differentiation.

General Definitions

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifugation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting [FACS]). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

In a specific embodiment, the term "about" or "approximately" means within 20%, preferably within 10%, and more preferably within 5% of a given value or range.

A "sample" as used herein refers to a biological material which can be tested for the presence of Ozz protein or Ozz nucleic acids. Such samples can be obtained from animal subjects, such as humans and non-human animals, and include tissue, especially muscle, biopsies, blood and blood products (plasma and serum, e.g., for released Ozz protein; or blood cells, particularly nucleated cells, for possible detection of protein or nucleic acids); plural effusions; cerebrospinal fluid (CSF); ascites fluid; and cell culture.

Non-human animals include, without limitation, laboratory animals such as mice, rats, rabbits, hamsters, guinea pigs, etc.; domestic animals such as dogs and cats; and, farm animals such as sheep, goats, pigs, horses, and cows.

The use of italics indicates a nucleic acid molecule (e.g., Ozz cDNA, gene, etc.); normal text indicates the polypeptide or protein.

Thus, the present invention advantageously provides Ozz protein, including fragments, derivatives, and analogs of Ozz; Ozz nucleic acids, including oligonucleotide primers and probes, and Ozz regulatory sequences; Ozz-specific antibodies; and related methods of using these materials to detect the presence of Ozz proteins or nucleic acids, Ozz binding partners, and in screens for agonists and antagonists of Ozz. The following sections of the application, which are delineated by headings (in bold) and sub-headings (in bold italics), which cover these aspects of the invention, are provided for clarity, and not by way of limitation.

Ozz

Figure 5:
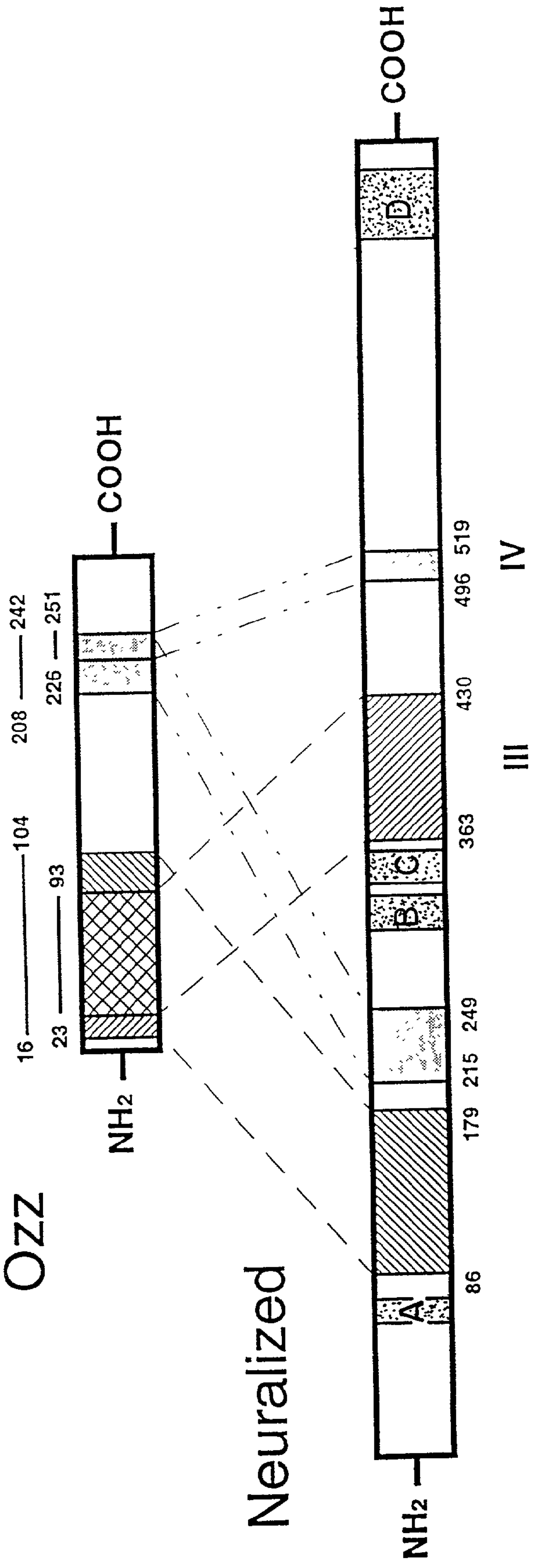
FIG. 5. Schematic representation of the Ozz and neuralized proteins, showing regions of homology between the two primary sequences.

Ozz protein, as defined herein, refers to a polypeptide having about 285 amino acids. In a specific embodiment, human Ozz has 285 amino acids. In another specific embodiment, murine Ozz also has 285 amino acids. Ozz can have a calculated molecular weight of about 31.5 kilo-Daltons (kDa); when murine Ozz is expressed in a recombinant cell line, for example, the apparent molecular weight is about 29–30 kDa, as measured by SDS-polyacrylamide gel electrophoresis. Because they are highly homologous, human Ozz can be expected to have very similar properties. Indeed, human and murine Ozz share 90% sequence identity, and 92% sequence similarity. Thus, the term Ozz encompasses polypeptides having about 90% sequence identity or about 92% sequence similarity with SEQ ID NO:2 or 4 (murine or human Ozz). The N-terminal portion of Ozz has significant homology with Neuralized protein. In a specific embodiment, there is about 40% sequence identity between the N-terminal portion of Ozz and a duplicated repeat of *Drosophila* neuralized protein. In addition, there is a stretch of about 30 amino acids at the C-terminus of Ozz that shows homology to two regions of neuralized protein. In a specific embodiment, the regions of homology of both the N-terminal and C-terminal regions of Ozz with *Drosophila* neuralized are shown in FIGS. 5 and 6.

Ozz can be further characterized by a tissue-specific expression pattern. Both Ozz mRNA and Ozz protein are only observed in heart and skeletal muscle, using routine assays (Northern analysis for mRNA and Western analysis for protein). This tissue-specific expression pattern has been observed for both mice and humans. It has also been found to be expressed in mice starting at embryonic day 12.5 (E12.5).

Ozz can also be characterized by the proteins to which it binds. In specific embodiments, using a yeast two-hybrid screen, Ozz was found to associate with β-catenin, myosin, c-Nap, and Alix proteins. Further evidence of Ozz association with β-catenin was found by co-immunoprecipitation analysis. In another embodiment, Ozz binds to an Ozz-specific antibody, e.g., as exemplified below.

In a specific embodiment, in order to develop the specific C-terminal and N-terminal Ozz antibodies, antibodies can be raised against the two halves of Ozz protein. The two peptides are produced from two truncated forms of mouse Ozz cDNA (corresponding to the nt 1-483 and nt 478-1036, respectively) fused with the GST coding sequence. The N terminus has neuralized homology.

Ozz fragments, derivatives, and analogs can be characterized by one or more of the characteristics of Ozz protein. For example, an Ozz fragment, also termed herein an Ozz peptide or polypeptide, can have an amino acid sequence corresponding to a homology region of neuralized protein, and in particular one of the fragments having SEQ ID NO:5, 7, 9, or 11 (the homologous fragments of Ozz shown in FIG. 6). In addition, an Ozz peptide can have an amino acid sequence of the SOCS box having the sequence PSLQT LCRLVIQRSMVHRLAIDGLHLPKELKDFCKYE (SEQ ID NO:23), or the amino acid sequence of a BC box having the sequence SLxxxCxxxI (SEQ ID NO:24). In another embodiment, an Ozz fragment comprises a putative phosphorylation site, e.g., a site for casein II (in a specific embodiment, such as site has a sequence as depicted in SEQ ID NO:19), protein kinase C (in a specific embodiment, such a site has a sequence as depicted in SEQ ID NO:20), or tyrosine kinase (in a specific embodiment, such a site has a sequence as depicted in SEQ ID NO:22). In yet another embodiment, an Ozz fragment can contain an alternative modification site, for example a myristoylation site (in a specific embodiment, such a site has a sequence as depicted in SEQ ID NO:21).

Analogs and derivatives of Ozz of the invention have the same or homologous characteristics of Ozz as set forth above. For example, a truncated form of Ozz can be provided. Such a truncated form includes Ozz with a deletion. In a specific embodiment, the derivative is functionally active, i.e., capable of exhibiting one or more functional activities associated with a full-length, wild-type Ozz of the invention. Such functions include binding β-catenin.

Alternatively, an Ozz chimeric fusion protein can be prepared in which the Ozz portion of the fusion protein has one or more characteristics of Ozz. Such fusion proteins include fusions of Ozz polypeptide with a marker polypeptide, such as FLAG, a histidine tag, or, as exemplified herein, glutathione-S-transferase (GST). Ozz can also be fused with a unique phosphorylation site for labeling. In another embodiment, Ozz can be expressed as a fusion with a bacterial protein, such as β-galactosidase.

Ozz analogs can be made by altering encoding nucleic acid sequences by substitutions, additions or deletions that provide for functionally similar molecules, i.e., molecules that perform one or more Ozz functions. In a specific embodiment, an analog of Ozz is a sequence-conservative variant of Ozz. In another embodiment, an analog of Ozz is a function-conservative variant. In yet another embodiment, an analog of Ozz is an allelic variant or a homologous variant from another species. In a specific embodiment, human and murine variants of Ozz are described.

Ozz derivatives include, but are by no means limited to, phosphorylated Ozz, myristylated Ozz, methylated Ozz, and other Ozz proteins that are chemically modified. Ozz derivatives also include labeled variants, e.g., radio-labeled with iodine (or, as pointed out above, phosphorous); a detectable molecule, such as but by no means limited to biotin, a chelating group complexed with a metal ion, a chromophore or fluorophore, a gold colloid, or a particle such as a latex bead; or attached to a water soluble polymer.

Chemical modification of biologically active component or components of Ozz may provide additional advantages under certain circumstances, such as increasing the stability and circulation time of the component or components and decreasing immunogenicity. See U.S. Pat. No. 4,179,337, Davis et al., issued Dec. 18, 1979. For a review, see Abuchowski et al., in Enzymes as Drugs (J. S. Holcerberg and J. Roberts, eds. pp. 367–383 (1981)). A review article describing protein modification and fusion proteins is Francis, 1992, Focus on Growth Factors 3:4–10, Mediscript: Mountview Court, Friern Barnet Lane, London N20, OLD, UK.

The chemical moieties suitable for derivatization may be selected from among water soluble polymers. The polymer selected should be water soluble so that the component to which it is attached does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/component conjugate will be used therapeutically, and if so, the desired dosage, circulation time, resistance to proteolysis, and other considerations. For the present component or components, these may be ascertained using the assays provided herein.

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols and polyvinyl alcohol. Polyethylene glycol propionaldenhyde may advantages in manufacturing due to its stability in water.

Cloning and Expression of Ozz

The present invention contemplates analysis and isolation of a gene encoding a functional or mutant Ozz, including a full length, or naturally occurring form of Ozz, and any antigenic fragments thereof from any source, preferably human. It further contemplates expression of functional or mutant Ozz protein for evaluation, diagnosis, or therapy.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. ÊPerbal, *A Practical Guide To Molecular Cloning* (1984); F. M. Ausubel et al. (eds.), *Current Protocols in Molecular Biology*, John Wiley & Sons, Inc. (1994).

Molecular Biology—Definitions

"Amplification" of DNA as used herein denotes the use of polymerase chain reaction (PCR) to increase the concentration of a particular DNA sequence within a mixture of DNA sequences. For a description of PCR see Saiki et al., Science, 239:487, 1988.

"Chemical sequencing" of DNA denotes methods such as that of Maxam and Gilbert (Maxam-Gilbert sequencing, Maxam and Gilbert, Proc. Natl. Acad. Sci. USA, 74:560, 1977), in which DNA is randomly cleaved using individual base-specific reactions.

"Enzymatic sequencing" of DNA denotes methods such as that of Sanger (Sanger et al., 1977, Proc. Natl. Acad. Sci. USA, 74:5463, 1977), in which a single-stranded DNA is copied and randomly terminated using DNA polymerase, including variations thereof well-known in the art.

As used herein, "sequence-specific oligonucleotides" refers to related sets of oligonucleotides that can be used to detect allelic variations or mutations in the Ozz gene.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA)

formed by conjugating bases to an amino acid backbone. This also includes nucleic acids containing modified bases, for example thio-uracil, thio-guanine and fluoro-uracil.

The polynucleotides herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra.

Proteins and enzymes are made in the host cell using instructions in DNA and RNA, according to the genetic code. Generally, a DNA sequence having instructions for a particular protein or enzyme is "transcribed" into a corresponding sequence of RNA. The RNA sequence in turn is "translated" into the sequence of amino acids which form the protein or enzyme. An "amino acid sequence" is any chain of two or more amino acids. Each amino acid is represented in DNA or RNA by one or more triplets of nucleotides. Each triplet forms a codon, corresponding to an amino acid. For example, the amino acid lysine (Lys) can be coded by the nucleotide triplet or codon AAA or by the codon AAG. (The genetic code has some redundancy, also called degeneracy, meaning that most amino acids have more than one corresponding codon.) Because the nucleotides in DNA and RNA sequences are read in groups of three for protein production, it is important to begin reading the sequence at the correct amino acid, so that the correct triplets are read. The way that a nucleotide sequence is grouped into codons is called the "reading frame."

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" or "operatively associated with" of transcriptional and translational control sequences in a cell when RNA polymerase transcribes the coding sequence into mRNA, which is then trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.; they are discussed in greater detail below.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells and Baculovirus vectors, and mammalian host cells and vectors. In a specific embodiment, Ozz is expressed in COS-1 or $C_2C_{12}$ cells. Other suitable cells include CHO cells, HeLa cells, 293T (human kidney cells), mouse primary myoblasts, and NIH 3T3 cells.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is a such an element operatively associated with a different gene than the one it is operatively associated with in nature. In the context of the present invention, an Ozz gene is heterologous to the vector DNA in which it is inserted for cloning or expression, and it is heterologous to a host cell containing such a vector, in which it is expressed, e.g., a CHO cell.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90 or 95%) of the nucleotides match over the defined length of the DNA sequences, as determined by sequence comparison algorithms, such as BLAST, FASTA, DNA Strider, etc. An example of such a sequence is an allelic or species variant of the specific Ozz genes of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.)

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nt in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nt; preferably at least about 15 nt; and more preferably the length is at least about 20 nt.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nt, preferably no more than 100 nt, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of Ozz, or to detect the presence of nucleic acids encoding Ozz. In a further embodiment, an oligonucleotide of the invention can form a triple helix with a Ozz DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

The present invention provides antisense nucleic acids (including ribozymes), which may be used to inhibit expression of Ozz of the invention, particularly to suppress Ozz regulation of β-catenin. An "antisense nucleic acid" is a single stranded nucleic acid molecule which, on hybridizing under cytoplasmic conditions with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607).

Specific non-limiting examples of synthetic oligonucleotides envisioned for this invention include oligonucleotides that contain phosphorothioates, phosphotriesters, methyl phosphonates, short chain alkyl, or cycloalkl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—$PO_2$—O—$CH_2$). U.S. Pat. No. 5,677,437 describes heteroaromatic olignucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substitued silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties.

Oligonucleotides may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an oligonucleotide molecule.

Ozz Nucleic Acids

A gene encoding Ozz, whether genomic DNA or cDNA, can be isolated from any source, particularly from a human cDNA or genomic library. Methods for obtaining Ozz gene are well known in the art, as described above (see, e.g., Sambrook et al., 1989, supra). The DNA may be obtained by standard procedures known in the art from cloned DNA (e.g., a DNA "library"), and preferably is obtained from a cDNA library prepared from tissues with high level expression of the protein (e.g., a muscle cell library, since these are the cells that evidence highest levels of expression of Ozz), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene. Identification of the specific DNA fragment containing the desired Ozz gene may be accomplished in a number of ways. For example, a portion of an Ozz gene exemplified infra can be purified and labeled to prepare a labeled probe, and the generated DNA may be screened by nucleic acid hybridization to the labeled probe (Benton and Davis, Science 196: 180, 1977; Grunstein and Hogness, Proc. Natl. Acad. Sci. U.S.A. 72:3961, 1975). Those DNA fragments with substantial homology to the probe, such as an allelic variant from another individual, will hybridize. In a specific embodiment, highest stringency hybridization conditions are used to identify a homologous Ozz gene.

Further selection can be carried out on the basis of the properties of the gene, e.g., if the gene encodes a protein product having the isoelectric, electrophoretic, amino acid composition, partial or complete amino acid sequence, antibody binding activity, or ligand binding profile of Ozz protein as disclosed herein. Thus, the presence of the gene may be detected by assays based on the physical, chemical, immunological, or functional properties of its expressed product.

Other DNA sequences which encode substantially the same amino acid sequence as an Ozz gene may be used in the practice of the present invention. These include but are not limited to allelic variants, species variants, sequence conservative variants, and functional variants.

Amino acid substitutions may also be introduced to substitute an amino acid with a particularly preferable property. For example, a Cys may be introduced a potential site for disulfide bridges with another Cys.

The genes encoding Ozz derivatives and analogs of the invention can be produced by various methods known in the art. The manipulations which result in their production can occur at the gene or protein level. For example, the cloned Ozz gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of Ozz, care should be taken to ensure that the modified gene remains within the same translational reading frame as the Ozz gene, uninterrupted by translational stop signals, in the gene region where the desired activity is encoded.

Additionally, the Ozz-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Such modifications can be made to introduce restriction sites and facilitate cloning the Ozz gene into an expression vector. Any technique for mutagenesis known in the art can be used, including but not limited to, in vitro site-directed mutagenesis (Hutchinson, C., et al., J. Biol. Chem. 253:6551, 1978; Zoller and Smith, DNA 3:479–488, 1984; Oliphant et al., Gene 44:177, 1986; Hutchinson et al., Proc. Natl. Acad. Sci. U.S.A. 83:710, 1986), use of TAB linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences.

Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2m plasmid.

Ozz Regulatory Nucleic Acids

A particular advantage of the present invention is the identification of the heart and muscle-specific promoter of Ozz. This discovery has important implications in the field of gene therapy, since therapeutic vectors, as described in the sub-section entitled "Vectors", infra, can be modified to employ the Ozz promoter for tissue-specific expression of a therapeutic protein. For example, expression of an angiogenic factor, such as basic fibroblast growth factor, VEGF, VEGf2, angiopoietin, etc., can be limited to target ischemic muscle (heart or skeletal muscle).

Ozz appears to share the PPCA proximal promoter (see FIG. 3), which contains three E-boxes. These E-boxes, which can function in either orientation, are target sites for muscle-specific transcription factors belonging to the Myo-D family. (It is, therefore, surprising to find them in the PPCA promoter, since PPCA is expressed ubiquitously). Other elements of the Ozz promoter can be identified by scanning the human genomic region upstream of the Ozz start site, e.g., by creating deletion mutants and checking for expression, or with the TRANSFAC algorithm. Sequences up to about 6 kb or more upstream from the Ozz start site can contain tissue-specific regulatory elements. In particular, in intron X of the human PPGB gene (the human homolog of murine PPCA), at 5.5 kb and 4.5 kb upstream of the Ozz start site, recognition sites for a cardiac-specific transcription factor nkxc-2.5 characterized in mouse (Chen, et al., J. Biol. Chem., 270:15628–33, 1995) have been identified. These may function to regulate tissue-specific expression of Ozz.

The term “Ozz promoter” encompasses artificial promoters. Such promoters can be prepared by deleting non-essentially intervening sequences from the upstream region of the Ozz promoter, or by joining upstream regulatory elements from the Ozz promoter with a heterologous minimal promoter, such as the CMV immediate early promoter.

Expression of Ozz Polypeptides

The nucleotide sequence coding for Ozz, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Thus, a nucleic acid encoding Ozz of the invention can be operationally associated with a promoter in an expression vector of the invention. Both cDNA and genomic sequences can be cloned and expressed under control of such regulatory sequences. Such vectors can be used to express functional or functionally inactivated Ozz polypeptides.

The necessary transcriptional and translational signals can be provided on a recombinant expression vector, or they may be supplied by the native gene encoding Ozz and/or its flanking regions.

Potential host-vector systems include but are not limited to mammalian cell systems transfected with expression plasmids or infected with virus (e.g., vaccinia virus, adenovirus, adeno-associated virus, herpes virus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Expression of Ozz protein may be controlled by any promoter/enhancer element known in the art, but these regulatory elements must be functional in the host selected for expression. Promoters which may be used to control Ozz gene expression include, but are not limited to, cytomegalovirus (CMV) promoter, the SV40 early promoter region (Benoist and Chambon, 1981, Nature 290:304–310), the promoter contained in the 3' long terminal repeat of Rous sarcoma virus (Yamamoto, et al., Cell 22:787–797, 1980), the herpes thymidine kinase promoter (Wagner et al., Proc. Natl. Acad. Sci. U.S.A. 78:1441–1445, 1981), the regulatory sequences of the metallothionein gene (Brinster et al., Nature 296:39–42, 1982); prokaryotic expression vectors such as the b-lactamase promoter (Villa-Komaroff, et al., Proc. Natl. Acad. Sci. U.S.A. 75:3727–3731, 1978), or the tac promoter (DeBoer, et al., Proc. Natl. Acad. Sci. U.S.A. 80:21–25, 1983); see also “Useful proteins from recombinant bacteria” in Scientific American, 242:74–94, 1980; promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Mogram et al., Nature 315:338–340, 1985; Kollias et al., Cell 46:89–94, 1986), hematopoietic stem cell differentiation factor promoters, erythropoietin receptor promoter (Maouche et al., Blood, 15:2557, 1991), etc.

Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

Vectors

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMal-C2, pET, pGEX (Smith et al., Gene 67:31–40, 1988), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2m plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences; and the like.

Preferred vectors are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional or mutant Ozz protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques, 7:980–990, 1992). Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV 1) vector (Kaplitt et al., Molec. Cell. Neurosci. 2:320–330, 1991), defective herpes virus vector lacking a glyco-protein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al. (J. Clin. Invest. 90:626–630, 1992; see also La Salle et al., Science 259:988–990, 1993); and a defective adeno-associated virus vector (Samulski et al., J. Virol. 61:3096–3101, 1987; Samulski et al., J. Virol. 63:3822–3828, 1989; Lebkowski et al., Mol. Cell. Biol. 8:3988–3996, 1988).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), Intro Gene (Lei den, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-g (IFN-g), or anti-CD4 antibody, can be administered to block humoral or cellular immune responses to the viral vectors (see, e.g., Wilson, Nature Medicine, 1995). In that regard, it is advantageous to employ a viral vector that is engineered to express a minimal number of antigens.

Ozz Binding Partners

The present invention further permits identification of physiological binding partners of Ozz. For example, as shown below, the invention exemplifies reagents to investigate the interaction between Ozz and β-catenin. Similar experiments can be done with myosin and the less known c-Nap and Alix, in order to understand their possible role in the Ozz pathway.

One method for evaluating and identifying Ozz binding partners is the yeast two-hybrid screen. Preferably, the yeast two-hybrid screen would be performed using a muscle cell library with yeast that are transformed with recombinant Ozz, e.g., as shown in the Example, infra. Alternatively, Ozz can be used as a capture or affinity purification reagent. Again, the preferred source material for such preparations is muscle cells. In another alternative, labeled Ozz can be used as a probe for binding, e.g., immunoprecipitation or Western analysis.

Generally, binding interactions between Ozz and any of its binding partners will be strongest under conditions approximating those found in the cytoplasm, i.e., physiological conditions of ionic strength, pH and temperature. Perturbation of these conditions will tend to disrupt the stability of a binding interaction.

Antibodies to Ozz

Antibodies to Ozz are useful, inter alia, for diagnostics and intracellular regulation of Ozz activity, as set forth below. According to the invention, Ozz polypeptides produced recombinantly or by chemical synthesis, and fragments or other derivatives or analogs thereof, including fusion proteins, may be used as an immunogen to generate antibodies that recognize the Ozz polypeptide. Such antibodies include but are not limited to polyclonal, monoclonal, chimeric, single chain, Fab fragments, and an Fab expression library. Such an antibody is specific for human Ozz; it may recognize a mutant form of Ozz, or wild-type Ozz.

Various procedures known in the art may be used for the production of polyclonal antibodies to Ozz polypeptide or derivative or analog thereof. For the production of antibody, various host animals can be immunized by injection with the Ozz polypeptide, or a derivative (e.g., fragment or fusion protein) thereof, including but not limited to rabbits, mice, rats, sheep, goats, etc. In one embodiment, the Ozz polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

For preparation of monoclonal antibodies directed toward the Ozz polypeptide, or fragment, analog, or derivative thereof, any technique that provides for the production of antibody molecules by continuous cell lines in culture may be used. These include but are not limited to the hybridoma technique originally developed by Kohler and Milstein (Nature 256:495–497, 1975), as well as the trioma technique, the human B-cell hybridoma technique (Kozbor et al., Immunology Today 4:72, 1983; Cote et al., Proc. Natl. Acad. Sci. U.S.A. 80:2026–2030, 1983), and the EBV-hybridoma technique to produce human monoclonal antibodies (Cole et al., in Monoclonal Antibodies and Cancer Therapy, Alan R. Liss, Inc., pp. 77–96, 1985). In an additional embodiment of the invention, monoclonal antibodies can be produced in germ-free animals (International Patent Publication No. WO 89/12690, published Dec. 28, 1989). In fact, according to the invention, techniques developed for the production of "chimeric antibodies" (Morrison et al., J. Bacteriol. 159:870, 1984); Neuberger et al., Nature 312:604–608, 1984; Takeda et al., Nature 314:452–454, 1985) by splicing the genes from a mouse antibody molecule specific for an Ozz polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

According to the invention, techniques described for the production of single chain antibodies (U.S. Pat. Nos. 5,476,786 and 5,132,405 to Huston; U.S. Pat, No. 4,946,778) can be adapted to produce Ozz polypeptide-specific single chain antibodies. An additional embodiment of the invention utilizes the techniques described for the construction of Fab expression libraries (Huse et al., Science 246:1275–1281, 1989) to allow rapid and easy identification of monoclonal Fab fragments with the desired specificity for an Ozz polypeptide, or its derivatives, or analogs.

In the production and use of antibodies, screening for or testing with the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an Ozz polypeptide, one may assay generated hybridomas for a product which binds to an Ozz polypeptide fragment containing such epitope. For selection of an antibody specific to an Ozz polypeptide from a particular species of animal, one can select on the basis of positive binding with Ozz polypeptide expressed by or isolated from cells of that species of animal.

The foregoing antibodies can be used in methods known in the art relating to the localization and activity of the Ozz polypeptide, e.g., for Western blotting, imaging Ozz polypeptide in situ, measuring levels thereof in appropriate physiological samples, etc. using any of the detection techniques mentioned above or known in the art. Such antibodies can also be used in assays for ligand binding, e.g., as described in U.S. Pat. No. 5,679,582. Antibody binding generally occurs most readily under physiological conditions, e.g., pH of between about 7 and 8, and physiological ionic strength. The presence of a carrier protein in the buffer solutions stabilizes the assays. While there is some tolerance of perturbation of optimal conditions, e.g., increasing or decreasing ionic strength, temperature, or pH, or adding detergents or chaotropic salts, such perturbations will decrease binding stability.

In a specific embodiment, antibodies that agonize or antagonize the activity of Ozz polypeptide can be generated. In particular, intracellular single chain Fv antibodies can be used to regulate (inhibit) Ozz. Such antibodies can be tested using the assays described infra for identifying ligands.

Screening and Chemistry

According to the present invention, nucleotide sequences derived from the gene encoding Ozz, and peptide sequences derived from Ozz, are useful targets to identify drugs that are effective in treating myogenesis disorders. Drug targets include without limitation (i) isolated nucleic acids derived from the gene encoding Ozz and (ii) isolated peptides and polypeptides derived from Ozz polypeptides.

In particular, identification and isolation of Ozz provides for development of screening assays, particularly for high throughput screening of molecules that up- or down-regulate the activity of Ozz, e.g., by permitting expression of Ozz in quantities greater than can be isolated from natural sources, or in indicator cells that are specially engineered to indicate the activity of Ozz expressed after transfection or transformation of the cells. Accordingly, the present invention contemplates methods for identifying specific ligands of Ozz using various screening assays known in the art.

Any screening technique known in the art can be used to screen for Ozz agonists or antagonists. The present invention contemplates screens for small molecule ligands or ligand analogs and mimics, as well as screens for natural ligands that bind to and agonize or antagonize Ozz in vivo. Such agonists or antagonists may, for example, interfere in the phosphorylation or dephosphorylation of Ozz, with resulting effects on Ozz function. For example, natural products libraries can be screened using assays of the invention for molecules that agonize or antagonize Ozz activity.

Knowledge of the primary sequence of Ozz, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith, Science 249:386–390, 1990; Cwirla, et al., Proc. Natl. Acad. Sci., 87:6378–6382, 1990; Devlin et al., Science, 49:404–406, 1990), very large libraries can be constructed ($10^6$–$10^8$ chemical entities). A second approach uses primarily chemical methods, of which the Geysen method (Geysen et al., Molecular Immunology 23:709–715, 1986; Geysen et al. J. Immunologic Method 102:259–274, 1987; and the method of Fodor et al. (Science 251:767–773, 1991) are examples. Furka et al. (14th International Congress of Biochemistry, Volume #5, Abstract FR:013, 1988; Furka, Int. J. Peptide Protein Res. 37:487–493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al., Proc. Natl . Acad. Sci. USA 90:10700–4, 1993; Ohlmeyer et al., Proc. Natl. Acad. Sci. USA 90:10922–10926, 1993; Lam et al., International Patent Publication No. WO 92/00252; Kocis et al., International Patent Publication No. WO 9428028) and the like can be used to screen for Ozz ligands according to the present invention.

Test compounds are screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., Tib Tech, 14:60, 1996).

In Vivo Screening Methods

Intact cells or whole animals expressing a gene encoding Ozz can be used in screening methods to identify candidate drugs.

In one series of embodiments, a permanent cell line is established. Alternatively, cells (including without limitation mammalian, insect, yeast, or bacterial cells) are transiently programmed to express an Ozz gene by introduction of appropriate DNA or mRNA. Identification of candidate compounds can be achieved using any suitable assay, including without limitation (i) assays that measure selective binding of test compounds to Ozz (ii) assays that measure the ability of a test compound to modify (i.e., inhibit or enhance) a measurable activity or function of Ozz and (iii) assays that measure the ability of a compound to modify (i.e., inhibit or enhance) the transcriptional activity of sequences derived from the promoter (i.e., regulatory) regions the Ozz gene.

Ozz knockout mammals can be prepared for evaluating the molecular pathology of this defect in greater detail than is possible with human subjects. Such animals also provide excellent models for screening drug candidates. A "knockout mammal" is an mammal (e.g., mouse) that contains within its genome a specific gene that has been inactivated by the method of gene targeting (see, e.g., U.S. Pat. Nos. 5,777,195 and 5,616,491). A knockout mammal includes both a heterozygote knockout (i.e., one defective allele and one wild-type allele) and a homozygous mutant (i.e., two defective alleles; however, in this case a heterologous construct for expression of an Ozz, such as a human Ozz, would be inserted to permit the knockout mammal to live). Preparation of a knockout mammal requires first introducing a nucleic acid construct that will be used to suppress expression of a particular gene into an undifferentiated cell type termed an embryonic stem cell. This cell is then injected into a mammalian embryo. A mammalian embryo with an integrated cell is then implanted into a foster mother for the duration of gestation. Zhou, et al. (Genes and Development, 9:2623–34, 1995) describes PPCA knock-out mice.

The term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise 1) a full or partial sequence of one or more exons and/or introns of the gene to be suppressed, 2) a full or partial promoter sequence of the gene to be suppressed, or 3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo.

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

Generally, the DNA will be at least about 1 kilobase (kb) in length and preferably 3–4 kb in length, thereby providing sufficient complementary sequence for recombination when the knockout construct is introduced into the genomic DNA of the ES cell (discussed below).

Included within the scope of this invention is a mammal in which two or more genes have been knocked out. Such mammals can be generated by repeating the procedures set forth herein for generating each knockout construct, or by breeding to mammals, each with a single gene knocked out, to each other, and screening for those with the double knockout genotype.

Regulated knockout animals can be prepared using various systems, such as the tet-repressor system (see U.S. Pat. No. 5,654,168) or the Cre-Lox system (see U.S. Pat. Nos. 4,959,317 and 5,801,030).

In another series of embodiments, transgenic animals are created in which (i) a human Ozz is stably inserted into the genome of the transgenic animal; and/or (ii) the endogenous Ozz genes are inactivated and replaced with human Ozz genes. See, e.g., Coffman, Semin. Nephrol. 17:404, 1997; Esther et al., Lab. Invest. 74:953, 1996; Murakami et al., Blood Press. Suppl. 2:36, 1996. Such animals can be treated with candidate compounds and monitored for muscle weakness, heart defects, or other indicia of muscle dysfunction.

High-Troughput Screen

Agents according to the invention may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time. Such high-throughput screening methods are particularly preferred. The use of high-throughput screening assays to test for agents is greatly facilitated by the availability of large amounts of purified polypeptides, as provided by the invention.

Methods of Diagnosis

According to the present invention, genetic variants of Ozz can be detected to diagnose a muscle degenerative disease. The various methods for detecting such variants are described herein. Where such variants impact Ozz function, either as a result of a mutated amino acid sequence or because the mutation results in expression of a truncated protein, or no expression at all, they are expected to result in disregulation of muscle development or function, including, possibly, muscle degeneration or alternatively hyperproliferation (e.g., a muscle sarcoma). In another embodiment, the presence of Ozz in blood or a blood fraction (serum, plasma) indicates muscle tissue damage, e.g., ischemia associated with either unstable angina, myocardial infarction, or both (see U.S. Pat. Nos. 5,747,274 and 5,744,358).

According to the present invention, altered Ozz protein levels and localization can be detected to diagnose diseases associated with altered Ozz protein expression and localization. The methods for detecting such altered protein levels and protein are described herein. When altered protein levels or protein localization are detected, they are expected to be associated with disease states that occur with altered Ozz expression. In one specific embodiment, the altered Ozz protein expression and localization is associated with galactosialidosis. In another embodiment, the altered protein levels or localization are evaluated with muscle cells that are from the atrium of the heart.

A "sample" as used herein refers to a biological sample, such as, for example, tissue (or cells) or fluid isolated from an individual or from in vitro cell culture constituents, as well as samples obtained from the environment or laboratory procedures. Non-limiting examples of cell sources available in clinical practice include without limitation muscle biopsies.

Nucleic Acid Assays

The DNA may be obtained from any cell source. DNA is extracted from the cell source or body fluid using any of the numerous methods that are standard in the art. It will be understood that the particular method used to extract DNA will depend on the nature of the source. Generally, the minimum amount of DNA to be extracted for use in the present invention is about 25 pg (corresponding to about 5 cell equivalents of a genome size of $4\times10^9$ base pairs). Sequencing methods are described in detail, supra.

In another alternate embodiment, RNA is isolated from biopsy tissue using standard methods well known to those of ordinary skill in the art such as guanidium thiocyanate-phenol-chloroform extraction (Chomocyznski et al., Anal. Biochem., 162:156, 1987). The isolated RNA is then subjected to coupled reverse transcription and amplification by polymerase chain reaction (RT-PCR), using specific oligonucleotide primers that are specific for a selected site. Conditions for primer annealing are chosen to ensure specific reverse transcription and amplification; thus, the appearance of an amplification product is diagnostic of the presence of a particular genetic variation. In another embodiment, RNA is reverse-transcribed and amplified, after which the amplified sequences are identified by, e.g., direct sequencing. In still another embodiment, cDNA obtained from the RNA can be cloned and sequenced to identify a mutation.

Protein Assays

In an alternate embodiment, biopsy tissue is obtained from a subject. Antibodies that are capable of specifically binding to Ozz are then contacted with samples of the tissue to determine the presence or absence of a Ozz polypeptide specified by the antibody. The antibodies may be polyclonal or monoclonal, preferably monoclonal. Measurement of specific antibody binding to cells may be accomplished by any known method, e.g., quantitative flow cytometry, enzyme-linked or fluorescence-linked immunoassay, Western analysis, etc.

Immunoassay technology, e.g., as described in U.S. Pat. Nos. 5,747,274 and 5,744,358, and particularly solid phase "chromatographic" format immunoassays, are preferred for detecting proteins in blood or blood fractions.

EXAMPLES

The present invention will be better understood by reference to the following Examples, which are provided by way of exemplification and not by way of limitation.

Example 1

Discovery of Ozz

Through the analysis of the 5' regions of the murine PPCA gene, we identified a new transcriptional unit that overlaps with exon Ia of the murine PPCA gene and is transcribed from the opposite strand. The resulting 1.0 kb mRNA is preferentially expressed in the heart and skeletal muscle, and encodes a protein of 285 amino acids that shares significant homology with the *Drosophila* neuralized gene. We have termed this new protein Ozz.

Materials and Methods

Cloning. A murine heart poly $A^+$cDNA library was obtained from Clontech and screened by hybridization at high stringency (last washing step was 65° C. with 0.1% of SSC) according to the manufacturer's protocol with the PPCA exon Ia as a probe. Double positives were rescreened with the same probe and a PPCA cDNA fragment. Phages that were only positive for the exon Ia probe were further characterized. The isolated clones were subcloned into pBluescript II KS (Stratagene) using standard cloning techniques and sequenced with the Amersham thermocycler kit. A SalI fragment, containing the full length Ozz cDNA was subcloned into the eukaryotic expression vector pSCTOP, with or without the hemagglutinin tag. For the generation of GST-Ozz fusion proteins we used the pGEX4T-2 plasmid from Pharmacia using standard restriction and ligation procedures.

Northern blot analysis. Northern blots containing mRNAs from mouse tissues or different embryonal stages were purchased from Clontech and hybridized using the manufacturer's EXPRESSHYB mix and protocol.

Cell culture. COS-1 and $C_2C_{12}$ cells were cultured under standard conditions, using Dulbecco's Modified Eagle's Medium (DMEM) supplemented with antibiotics and 5–10% Fetal Bovine Serum (FBS). Primary mouse myoblasts were isolated from 3-day-old mice and were grown in medium consisting of Ham's F-10 nutrient mixture, 20% FBS and 2.5 ng/ml basic Fibroblast Growth Factor (bFGF). Primary myoblast and $C_2C_{12}$ were induced to form myotubes by replacing their growth medium with the differentiation medium (DMEM plus 2% horse serum for the myoblasts and DMEM plus Insulin Transferrin Selenite (ITS) for the $C_2C_{12}$ cells).

Antibody generation and purification. The full-length Ozz cDNA was subcloned into an inducible bacterial expression vector containing the glutathione S-transferase (GST) gene to generate antibodies in order to further characterize this novel gene product. The overexpressed GST-Ozz fusion protein was isolated using preparative SDS-PAGE and the purified electro-eluted protein was subcutaneously injected into rabbits to boost the production of anti-Ozz antibodies (made at Rockland Laboratories, Gilbertsville, Pa.). Rabbit serum was tested using protein extracts obtained from COS-1 cells transfected with the full-length Ozz cDNA.

The anti-Ozz antibodies were purified using bacterially overexpressed GST-Ozz protein. The fusion protein was purified by absorption with glutathione-agarose beads and then immobilized on AminoLink gel (PIERCE). The antiserum was passed through the column containing the Ozz protein and the bound antibodies were eluted.

Western blot analysis and immunoprecipitation. $C_2C_{12}$ and COS-1 cells were transfected with Qiagen's Superfect according to the manufacturer's procedures.

Protein extracts from mouse heart tissue were made by homogenizing the samples in four volumes of NP-40 buffer (50 mM Tris-HCl pH 7.5, 250 mM NaCl, 1 mM EDTA, 1% NP-40 and proteinase inhibitor). The protein concentration was measured with bicinchoninic acid (BCA) according to the manufacturer's protocol (Pierce Chemical Co.). Protein extracts from 10 adult mice hearts were subjected to gel filtration on a Sephacryl-300 HR and the FPLC fractions were collected. Both Ozz and β-catenin co-eluted around fraction 12 (about 500 kDa) as shown by probing Western blots of the eluted fractions with the corresponding antibodies (data not shown). For Western blot analysis, protein samples were resolved on 12.5% SDS-polyacrylamide gels, transferred to Immobilon PVDF membranes (Millipore) and probed with anti-βcatenin and anti-Ozz antibodies.

For the immunoprecipitation studies, transfected COS-1 and $C_2C_{12}$ cells were seeded in 85 mm Petri dishes and metabolically labeled for 16 hours with 350 μC*i* $^3$H-[4,5]-Leucine (Amersham). Radiolabeled proteins or FPLC fractions were immunoprecipitated with the indicated antibodies, as described previously (Proia, et al., J. Biol. Chem., 259:3350–54, 1984).

Yeast Two-Hybrid Screening. Standard PCR reactions were used to subclone the coding region of Ozz (845 bp) in frame with the GAL4 DNA-binding domain in the "bait" vector (pPC97). The yeast strain used in the two-hybrid screening was MAV103. Yeast transformations were made using the lithium acetate procedure (Ausubel, et al., *Current Protocols in Molecular Biology*, New York: John Wiley & Sons, Vol. 2, Ch. 13, 1994). MAV103 harboring the GAL4 DNA-binding domain-Ozz plasmid was further transformed with 1 μg of an oligo (dT)-primed 14 days embryo (head and ⅓ top of spine) mouse cDNA library cloned into the GAL4-activating domain vector (pPC86).

Double transformants were grown on Sc-Leu-Trp plates and subsequently replicaplated onto Sc-Leu-Trp-His containing 25 or 50 mM 3-Amino-1,2,4-Triazole (3-AT). After selection, transformants were re-screened on Sc-Leu-Trp-His+3AT (50 and 100 mM), on Sc-Leu-Trp-Ura and their ability to produce β-galactosidase was screened by the filter X-Gal assay (Chevray and Nathans, Proc. Natl. Acad. Sci. USA, 89:5789–93, 1992).

Results

Cloning a novel gene. Hybridization of a mouse multi-tissue Northern blot with PPCA exon Ia as a probe revealed the presence of a non-PPCA transcript of 1.0 kb, expressed primarily in mouse heart. The transcriptional orientation of the gene is opposite to that of the PPCA gene and completely overlaps with the exon Ia of PPCA (FIG. 1). Its corresponding cDNA, isolated from a mouse heart library, included a short 5'UTR of 20 nt, an ATG start codon in a favorable Kozak context (Kozak, Mamm. Genome, 7:563–572, 1996), an open reading frame of 855 nt and a 3'UTR of 144 nt followed by a poly A tail of 17 adenosines (FIG. 2A). The cDNA is encoded by two exons, of 762 and 257 nt respectively, separated by an intron of at least 1.7 kb (FIG. 1).

The human genomic sequence of Ozz was identified by sequence comparison of the human locus corresponding to the murine PPCA locus. The corresponding human (syntenic) locus is termed PPGB, and is found on chromosome 20. The sequence of PPGB is found in NCBI database under accession number a1008726.

Figure 3A:
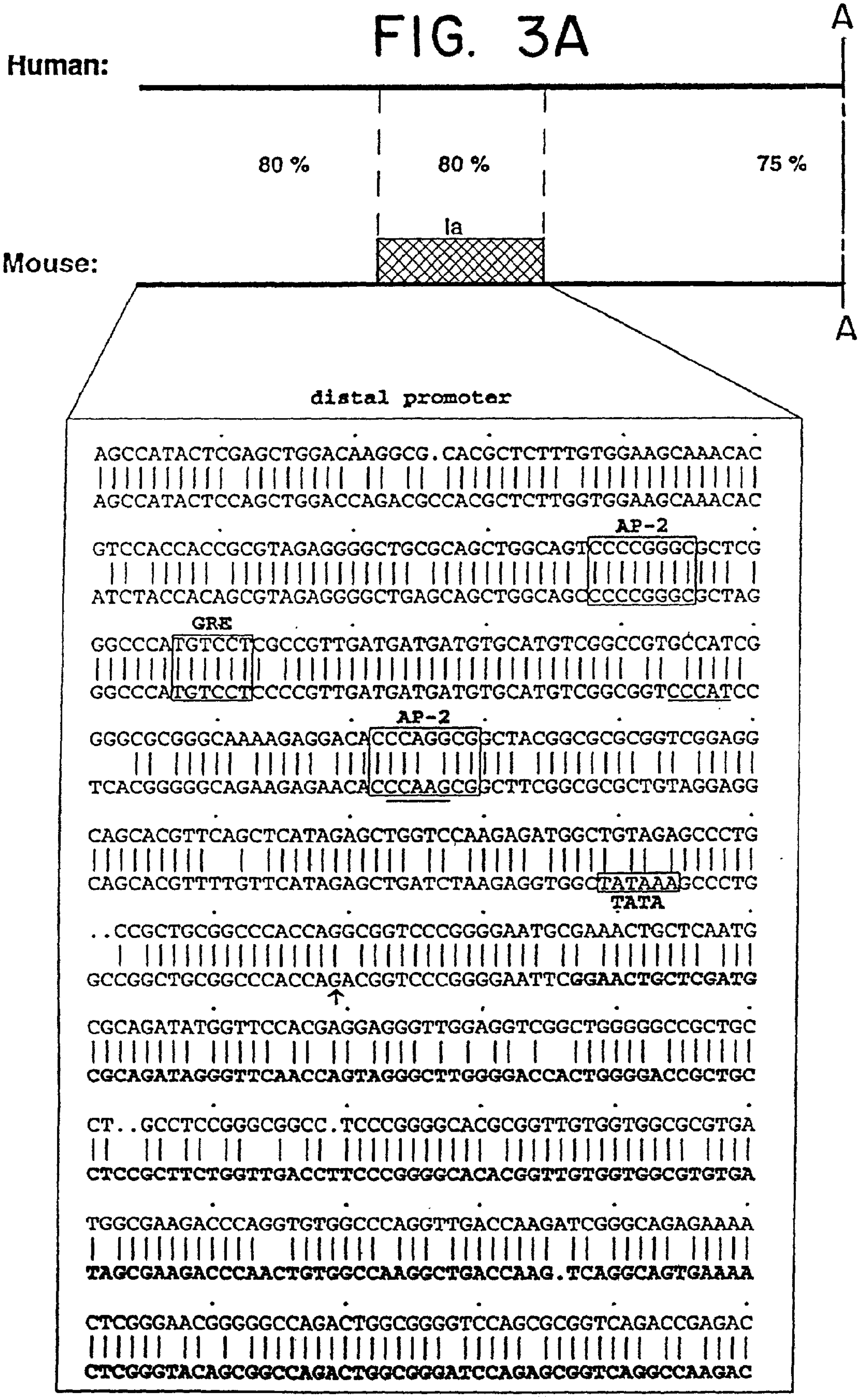
FIG. 3. Schematic representation of the human and mouse 5' genomic regions (top), and sequence comparison of their 5' UTRs and adjacent promoter regions (bottom; the human distal promoter is SEQ ID NO:13; the murine distal promoter is SEQ ID NO:14; the human proximal promoter is SEQ ID NOS:15 and 16; and the murine proximal promoter is SEQ ID NOS:17 and 18). Percentage of homology is indicated. The 5' UTR exons are in boldface and putative transcription factor binding sites are indicated. Two imperfect CAAT boxes are underlined in the murine distal promoter (bottom, left; SEQ ID NO:14). The transcriptional start sites, found by using RNase protection assays, are marked with an arrow above (human) or below (mouse) the sequence.
Figure 3B:
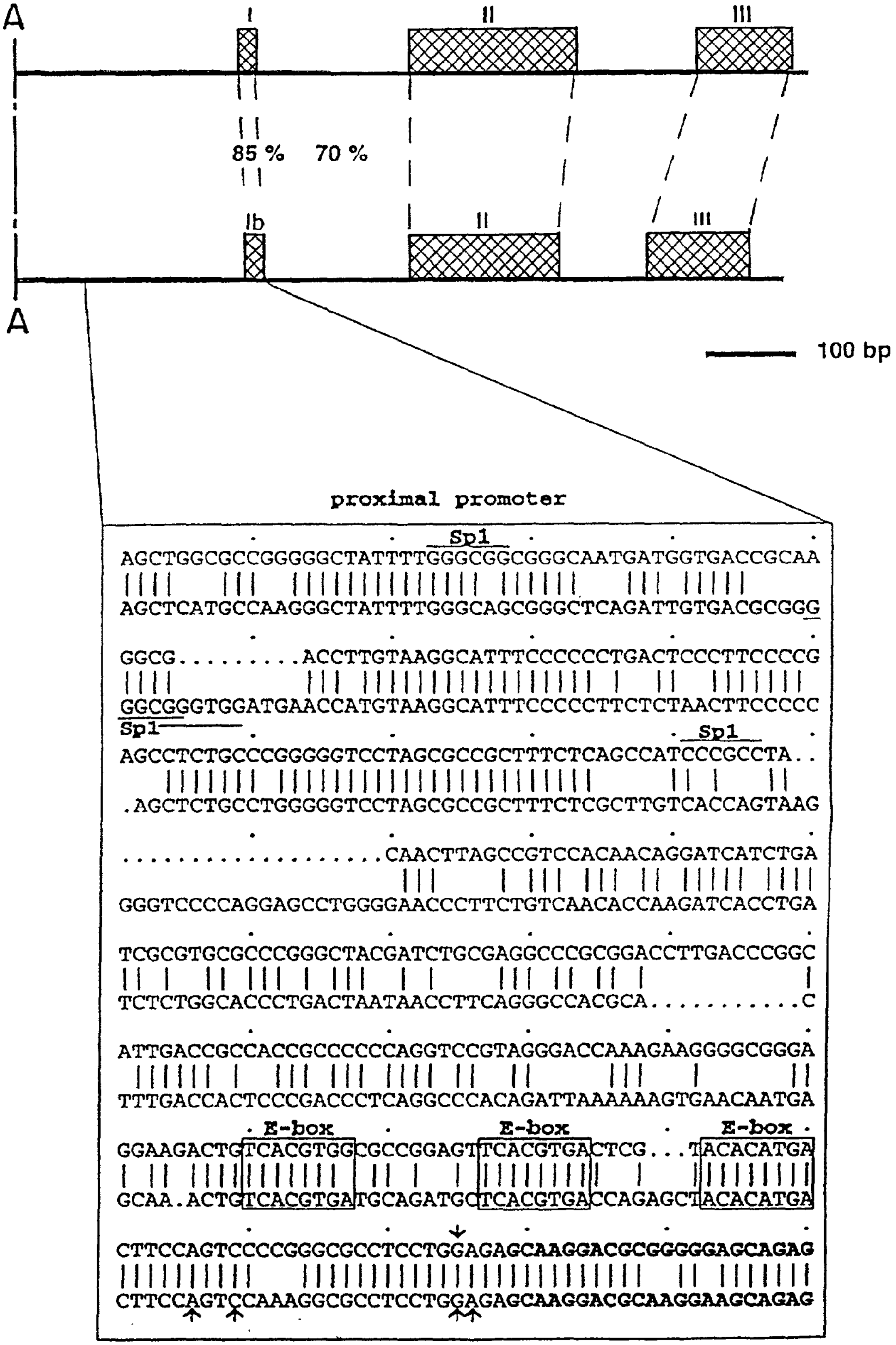

Specifically, sequence comparison of PPGB with the first exon of the cloned mouse Ozz DNA sequence permitted identification of the human homolog. The cDNA sequences of human (SEQ ID NO:3) and murine Ozz (SEQ ID NO:1) are highly homologous, with 85% sequence identity by BLASTN analysis (FIG. 3).

The cDNA (FIG. 2A, mouse and 2B, human) encodes a novel protein termed Ozz containing 285 amino acids with a calculated molecular weight of 31.5 kDa and a predicted isoelectric point at pH 8.15. The deduced amino acid sequence of human Ozz (SEQ ID NO:4) shows even greater homology to murine Ozz (SEQ ID NO:2). When analyzed by BLASTP analysis, these two proteins share 90% sequence identity and 92% sequence similarity (conservative amino acid substitutions). The comparison of these two sequences is shown in FIG. 4. Computer analysis of the protein sequence identified putative phosphorylation sites for casein kinase II, protein kinase C and tyrosine kinase, and three potential myristoylation sites (FIG. 4).

The C-terminus of Ozz is homologous to members of the CIS/SOCS/JAB/SSI family of cytokine inducible suppressor of cytokine signalling (SOCS) proteins. This homology is restricted to a region known as the SOCS box (Starr, et al. Nature, 387:917–921, 1997; Hilton et al. Proc. Natl. Sci. USA, 95:114–119, 1998). In the Ozz Sequence, the SOCS box has the amino acid sequence: PSLQTLCRLVIQRSMV HRLAIDGLHLPKELKDFCKYE (SEQ ID NO:23). In the described Ozz amino acid sequence, the bold amino acids are conserved between the Ozz protein and the SOCS box consensus sequence, the underlined amino acids represents positions that can accommodate any hydrophobic amino acid substitution, and the double underlined amino acids represents positions that can accommodate any amino acid substitution. The other residues vary within a limited number of choices.

Recent findings have suggested that the SOCS-box containing proteins are implicated in binding and in turn coupling specific substrate proteins to the ubiquitination/proteosomal pathway (Kamura, et al. Genes and Develop., 12:3872–3881, 1998; Zhang, et al., Proc. Natl. Acad. Sci. USA, 96:12436–12441, 1999), therefore controlling their intracellular turnover. This model is supported by the evidence of a direct interaction between SOCS proteins and component of the E3 ubiquitin ligase complexes. In particular, SOCS 3 was shown to bind to the Elongin B/C complex via a short consensus sequence present at the N-terminus of the SOCS box domain and called the BC box which has the consensus sequence of SLxxxCxxxI (SEQ ID NO:24). In the consensus sequence, this indicates that the serine position can be either serine or threonine, followed by a leucine or methionine, followed by any three amino acids, followed by cystine or serine, followed by any three amino acids, followed by valine, isoleucine, or leucine.

Data base searches for homologous proteins revealed a striking homology with the neuralized proteins of *Drosophila melanogaster* and *D. virilis* (Boulianne, et al., EMBO J., 2:2586–89, 1991; Price, et al., EMBO J., 12:2411–8, 1993; Zhou and Boulianne, Genome, 37:840–7,1994), as well as with the human and *C. elegans* homologs (Nakamura, et al., Oncogene, 16:1009–19, 1998). As seen in FIG. 5, the N-terminal 100 amino acids of the Ozz protein share 34–44% identity with the duplicated NHRs of neuralized proteins (*Neuralized Homology Repeat*, see FIGS. 5 and 6, and Nakamura, supra). Furthermore, a small stretch of about 30 amino acids, located at the C-terminus of Ozz bears homology to two regions of neuralized proteins, downstream of each of the two NHR domains. FIG. 6 shows the sequence alignment between the Ozz protein and *D. virilis* neuralized protein relative to the four homologous domains described earlier.

Northern blot hybridizatioin with Ozz. The expression pattern of Ozz in different adult mouse tissues was examined by Northern blot hybridization using the full-length cDNA as probe. Expression of the expected 1.0 kb Ozz transcript was confined to heart and skeletal muscle. The same expression pattern was observed in human RNA preparations from different tissues, where the 1 kb Ozz transcript was detected exclusively in heart and skeletal muscle, but not in the pancreas, kidney, liver, lung, placenta, or brain (FIG. 7).

It is indicative that the constitutive promoter of PPCA, which likely controls the transcription of the Ozz gene, contains three conserved E-boxes that are target sites for muscle-specific transcription factors belonging to the Myo-D family that control muscle development and differentiation (FIG. 3). In keeping with this observation, we found that Ozz mRNA starts to be detected in the embryo between day E12 and E15.

Protein expression. To gain insights into the precise timing and pattern of expression of the Ozz protein, as well as its physiological role, we raised monospecific polyclonal antibodies against a bacterially expressed full length protein fused to glutathion-S-transferase (GST-OZZ). These antibodies have been particularly useful for immunocytochemistry and immunoprecipitation studies.

Anti-Ozz antibodies were first tested for their ability to recognize the Ozz protein overexpressed in two different cell lines: COS-1 and $C_2C_{12}$ (the latter is a transformed mouse myoblast cell line). The antibodies immunoprecipitated a 29–30 kDa Ozz protein from both cell lines transfected with an Ozz cDNA construct (FIG. 8). The nature of the higher molecular weight band recognized by the Ozz antibodies in COS-1 cells is at the moment unclear.

Immunostaining of paraffin embedded sections of different mouse tissues clearly demonstrated a high level of expression of the protein in cardiac and skeletal muscle. These results confirmed the tissue distribution of the Ozz mRNA. In similar immunohystochemistry experiments, we could detect the Ozz protein in the mouse embryo as early as embryonal day 10 (E10). At this stage the protein is specifically expressed in the myotomes and in the developing heart. At E14.5, the protein is still detected in the developing heart and in the differentiating myofibers. In differentiating muscle fibers the strongest Ozz immunostining was seen in a region juxtaposed to the myotendinous region, as demonstrated by the co-staining with nestin a marker specific for the myotendinous junctions.

Effects on Ozz during in vitro differentiation. To elucidate the role of Ozz in muscle development and differentiation, we set up an inducible in vitro system, using both the transformed $C_2C_{12}$ muscle cell line as well as primary mouse myoblasts isolated from 3-day-old pups. Both cell types can be maintained in culture in an undifferentiated state and can be induced to differentiate by serum deprivation. The level of expression of Ozz was monitored during the differentiation process. In both instances the amount of Ozz protein sharply increased upon cell differentiation. This increase was particularly evident for the primary myoblasts. In the same cultures, we also followed the expression of markers specific for muscle differentiation (i.e. myogenin and myosin). The increase of Ozz expression coincided with the appearance of myosin and decrease of myogenin. Taken together these results point to the Ozz protein as a potential marker for terminal muscle differentiation, positioning it together with myosin downstream of the MyoD pathway.

Identification of Interacting Proteins. In order to identify possible partners of Ozz, that could contribute to or complement its function, we performed a yeast two-hybrid screening using the Ozz cDNA as a bait and a cDNA library from mouse embryonal stage E14.5. Four potentially interacting proteins were identified: β-catenin, myosin, c-Nap1 and Alix. In line with this initial observation we were able to detect Ozz, β-catenin and myosin in the same, high molecular weight fraction (407 kDa), after gel-filtration of crude extracts of adult mouse heart fractionated on an FPLC column. The interaction with β-catenin was confirmed by co-precipitation of Ozz with anti-β-catenin antibody from the 407-kDa FPLC fraction. The two proteins could also be co-precipitated from cell lysates of COS-1 cells transfected with both cDNA constructs.

The presence of a consensus BC-box at the N-terminus of the SOCS-box of Ozz (see FIG. 4) implied a possible interaction of Ozz with the Elongins B/C complex. To test this hypothesis, we co-expressed in 293T cells either a full-length Ozz cDNA or a mutant cDNA lacking the complete SOCS-box (Ozz) together with a Myc-tagged Elongin B and a HPC4-tagged Elongin C constructs. The ability of the expressed proteins to interact was assessed in co-immunoprecipitation assays. Ozz was readily co-precipitated with Elongin B, using a monoclonal anti-Myc antibody. This antibody did not co-precipitate the mutant Ozz protein, confirming that Ozz interacts with the Elongin B/C complex through the SOCS domain.

Ozz degradation. It has been suggested that the proteasome is involved in the degradation of SOCS proteins in hematopoietic cells (Kamura, T., et al., Genes and Develop., 12:3872–3881, 1998; Narazaki, et al., Proc. Natl. Acad. Sci. USA, 95:13130–13134, 1998). To determine whether the levels of Ozz protein during muscle differentiation are also modulated by the proteasome-pathway, primary myoblasts were cultured for 8 hours in the presence of 10 mM of lactacystin, a specific proteasome inhibitor. It has been reported that inhibition of the proteasome results in the accumulation of large protein aggregates that are recovered in an insoluble sub-cellular fraction. For this reason, after incubation with the inhibitor, muscle cell lysates were divided into a detergent-soluble and detergent-insoluble fractions. Ozz was barely detectable in untreated proliferating myoblasts but accumulated in the insoluble fraction after inhibition of the proteasome with lactacystin. Thus, in undifferentiated myoblasts Ozz is expressed but its intracellular concentration is maintained at low levels by a rapid turnover rate controlled by the proteasome. In contrast, in myotubes Ozz is only partially degraded by the proteasome as shown by the slight increase of Ozz protein in the insoluble fraction of lactacystin-treated myotube, compared to untreated cells. These data suggest that the synthesis and degradation of Ozz is tightly regulated during myogenesis and is dependent on the differentiation-state of the cells.

The intracellular distribution of the accumulated, detergent-insoluble pool of Ozz was further assessed by immunofluorescent staining of myoblast cultures, treated or untreated with lactacystin. For this purpose, primary myoblasts were infected with an MSCV-based bicistronic retroviral vector expressing Ozz cDNA and the green fluorescent protein (MSCV-OZZ-IRES-GFP) selectable marker. Infected cells were stained simultaneously with anti-Ozz and anti-myosin antibodies, used as marker of myoblast differentiation. Ozz accumulated in a large perinuclear aggregate in undifferentiated myoblasts; the size of this Ozz-positive structure was greatly reduced in the differentiated myotube. The perinuclear aggregate containing Ozz showed striking similarity to a recently described novel subcellular compartment, the aggresome (Johnston, et al., J. Cell Biol., 143: 1883–1898, 1998). Aggresome formation is believed to be a general response of cells to stress conditions and occurs when the production of aggregation-prone misfolded proteins saturates the proteasome capacity or when the proteasome is impaired.

These results suggest that during myogenesis Ozz undergoes post-translational regulation that affects its stability and results in the increase of endogenous Ozz after myoblast differentiation.

Proteasome-mediated degradation of Ozz. To ascertain the role of the interaction between Elongin B/C and Ozz in Ozz-stabilization, we infected primary myoblasts with the MSCV-OZZ-IRES-GFP retroviral vector as well as a similar vector virus carrying the deleted Ozz cDNA (MSCV-DOZZ-IRES-GFP). Wild type Ozz is expressed at significantly higher levels than the mutated Ozz although a comparable amount of GFP expression was obtained with the two vector. However, the level of DOzz protein increased considerably in the presence of the proteasome inhibitor, suggesting that the SOCS-box domain in the wild type protein is necessary to protect Ozz from the proteasome-induced degradation, possibly through the interaction with the Elongin B/C complex.

Ozz phosphorylation. To identify the signals influencing the stability of Ozz during in vitro myogenesis, we investigated the role of the putative tyrosine-phosphorylation site presents at the carboxy-terminus of the Ozz SOCS-box. We first tested whether Tyr284 was phosphorylated in NIH3T3 cells infected with two MSCV retroviruses carrying either the wild type or the mutated Ozz cDNA, used as control. Indeed the virus-encoded Ozz was phosphorylated since it could be detected with an anti-phosphotyrosine antibody only in cells infected with the wild type and not with the DOzz vector. Moreover, in primary myoblast cultures we were able to demonstrate that the endogenously expressed Ozz is tyrosine-phosphorylated only in the undifferentiated state, while in myotubes Ozz undergoes de-phosphorylation.

Taken together these observations raised the possibility that during myogenesis, phosphorylation of Tyr284 present in the SOCS-box may affect the interaction between Ozz and Elongin B/C, and in turn the stability of Ozz.

Ozz effects on intracellular β-catenin levels. It has been demonstrated that the multi-protein complex composed of Elongin B/C, the von Hippel-Lindau tumor-suppressor protein (pVHL), one of the cullins (Cul-2) and the Rbx-1 protein may function as an E3 ubiquitin-ligase that address pVHL-bound substrate proteins to proteasome-mediated degradation (Iwai, et al. Proc. Natl. Acad. Sci. USA, 96:12436–12441, 1999). It has also been postulated that the SOCS proteins represent a family of adapter molecules analogous to the pVHL, which could be involved, as pVHL, in targeting specific substrates to the proteasome degradative pathway. This hypothesis led us to examine whether perturbing Ozz expression in primary myoblasts may influence the stability of one of the Ozz interacting proteins, i.e. β-catenin. We found that in differentiated myotubes the mutant DOzz acts as a dominant-negative molecule on the endogenously expressed Ozz. Indeed, exogenous overexpression of DOzz caused an accumulation of β-catenin, although overexpression of wild type Ozz did not significantly influence β-catenin levels, probably because the system was already saturated.

Since the expression of mutant DOzz, which is unable to bind the Elongin B/C, perturbs the endogenous β-catenin levels, we can speculate that in the differentiated myotube Ozz targets its interacting substrate β-catenin to the proteasome pathway through interaction with the Elongin B/C.

Ozz expression in galactosialidosis. Given the genomic organization of the Ozz and PPCA genes, mutations affecting PPCA function and causing galactosialidosis could potentially influence or deregulate expression of Ozz as well. With this in mind we have tested the intracellular distribution and level of expression of the Ozz protein in autopsy specimens of the heart of an early infantile galactosialidosis patient with severe hypotonia and cardiac involvement. As mentioned earlier, immunostaining of adult mouse heart revealed a distribution of the protein in confined region of the atrial cardiomyocytes surrounding the nucleus. Using the anti-mouse Ozz antibodies we could confirm this subcellular distribution in cells from a normal human atrium. In contrast, cells from the atrium of the galactosialidosis patient showed an abnormal level and localization pattern of Ozz, suggesting that the mutation in the PPCA gene of this patient interfered with Ozz expression.

This finding helps with the interpretation phenotypic abnormalities affecting striated muscles and reported in some but not all patients with galactosialidosis. Furthermore, we can anticipate that deregulation of Ozz activity in the developing and/or differentiating muscle fibers may influence cellular homeostasis and in turn result in heart or skeletal muscle myopathies.

Discussion: Role of Ozz in Myogenesis

The crucial events in skeletal muscle differentiation are coordinated by the expression of muscle regulatory proteins acting in concert with the basic HLH transcription factors of the MyoD family. These transcription factors activate muscle-specific gene expression via their interaction with the E-box regulatory elements. The finding that the Ozz promoter contains three E-boxes correlates with its expression pattern in embryonal and adult tissues, and suggests that this protein may be critical in muscle differentiation.

The common sequence of myogenic events starts with the induction of the MyoD cascade (MyoD-myogenin-MRF4), followed by growth arrest, expression of structural sarcomeric components and finally fusion into myotubes. Myotube formation depends upon high cell density, whereas the expression of the different muscle-specific proteins can also be detected in subconfluent cell cultures, independently of the cell fusion.

Stable cell-cell interactions must be established between fusion-competent myoblasts as a prerequisite for further differentiation. Specific involvement of cadherins in this event has been suggested since N-cadherin is expressed at high levels in prefusion myoblasts and M-cadherin antibodies specifically inhibit myocyte fusion.

β-catenin is an intrinsic component of adherens junctions because it links cadherins via α-catenin to the actin cytoskeleton. However, β-catenin has been placed downstream of the Wnt and Wg signaling pathway and can translocate to the nucleus, where it transactivates target genes together with LEF and Tcf4 transcription factors. Variations in the level of β-catenin partners in these different cellular events can significantly modify or affect β-catenin signaling. On the basis of our data, Ozz protein appears to be a partner of β-catenin in muscle cells. Thus, modulation of Ozz activity in this cell system may regulate β-catenin stability, localization, and/or activity in normal myogenesis or combinations of these. Furthermore, because of β-catenin involvement in malignant transformation, mutations compromising Ozz activity may result in pathologic conditions, including impairing muscle function.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, are approximate, and are provided for description.

All patents, patent applications, publications, and other materials cited herein are hereby incorporated herein reference in their entireties.

What is claimed is:

1. An isolated nucleic acid encoding an Ozz protein wherein the Ozz protein is expressed only in cardiac and skeletal muscle, comprises about 285 amino acids, and shares about 90% sequence identity or about 92% sequence similarity with SEQ ID NO:2 or SEQ ID NO:4.

2. The nucleic acid of claim 1 which is a cDNA.

3. The nucleic acid of claim 1, wherein the Ozz protein is a mouse Ozz protein with a molecular weight of about 30 kilo-Daltons (kDa).

4. The nucleic acid of claim 3 which comprises a nucleotide sequence as depicted in SEQ ID NO:1.

5. A vector comprising a nucleic acid encoding a fragment of an Ozz protein operatively associated with an expression control sequence, wherein the fragment of an Ozz protein has the ability to bind a protein selected from the group consisting of β-catenin, myosin, c-Nap, and Alix; wherein full-length Ozz protein shares about 90% sequence identity or about 92% sequence similarity with SEQ ID NO:2 or SEQ ID NO:4 and comprises about 285 amino acids.

6. The vector according to claim 5, wherein the fragment of an Ozz protein is said full-length Ozz protein.

7. An isolated host cell transfected with the vector of claim 5.

8. A method for producing Ozz protein comprising isolating Ozz protein produced by the host cells of claim 7, wherein the host cells have been cultured under conditions that provide for expression of the Ozz protein by the vector.

9. An isolated nucleic acid consisting of at least ten consecutive nucleotides of SEQ ID NO: 1 or SEQ ID NO: 3 that hybridizes under stringent conditions with the nucleic acid having the nucleotide sequence of SEQ ID NO: 1 or SEQ ID NO: 3, with the proviso that the isolated nucleic acid is not a PPCA exon Ia, wherein the stringent conditions are hybridization at 68° C. in 0.2×SSC or 42° C. in 50% formamide, 4×SSC.

10. The nucleic acid of claim 1, wherein the Ozz protein is a human Ozz protein.

11. The nucleic acid molecule of claim 1, which comprises the nucleotide sequence of SEQ ID NO: 3.

* * * * *

UNITED STATES PATENT AND TRADEMARK OFFICE

CERTIFICATE OF CORRECTION

PATENT NO. : 7,074,908 B2
APPLICATION NO. : 10/014774
DATED : July 11, 2006
INVENTOR(S) : Alessandra D'azzo et al.

It is certified that error appears in the above-identified patent and that said Letters Patent is hereby corrected as shown below:

On Title Page, Item (75) Col. 1

Please delete "Antonella Bongiovanni, Memphis, TN (US)" and "Tommaso Nastasi, Memphis, TN (US)" and substitute with -- Antonella Bongiovanni, Palermo, Italy -- and -- Tommaso Nastasi, Monterotondo Scalo, Italy --.

Signed and Sealed this

Seventh Day of November, 2006

JON W. DUDAS
*Director of the United States Patent and Trademark Office*